(12) United States Patent
Chang et al.

(10) Patent No.: US 7,238,347 B2
(45) Date of Patent: Jul. 3, 2007

(54) SUICIDAL MUTANT *LEISHMANIA* VACCINE

(75) Inventors: Kwang-Poo Chang, Kenilworth, IL (US); Bala Krishna Kolli, Waukegan, IL (US); Shigeru Sassa, Tokyo (JP)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 11/091,882

(22) Filed: Mar. 28, 2005

(65) Prior Publication Data

US 2006/0018888 A1   Jan. 26, 2006

(51) Int. Cl.
  *A61K 48/00*   (2006.01)
  *A61K 39/08*   (2006.01)

(52) U.S. Cl. .............. 424/93.21; 424/269.1; 435/258.3; 435/476; 435/479

(58) Field of Classification Search ............... None
See application file for complete search history.

(56) References Cited

U.S. PATENT DOCUMENTS

2004/0092467 A1*   5/2004   Chang et al. ............ 514/44

OTHER PUBLICATIONS

Abels C, Fritsch C, Bolsen K, Szeimies RM, Ruzicka T, Goerz G, Goetz AE. Photodynamic therapy with 5-aminolaevulinic acid-induced porphyrins of an amelanotic melanoma in vivo. Journal of Photochemistry and Photobiology, B. Aug. 1997; 40(1):76-83.
Afonso SG, Chinarro S, Munoz JJ, de Salamanca RE, Battle AM. Photodynamic and non-photodynamic action of several porphyrins on the activity of some heme-enzymes, Journal of Enzyme Inhibitors. 1990; 3(4):303-10.
Ahmed SB, Bahloul C, Robbana C, Askri S, Dellagi K. A comparative evaluation of different DNA vaccine candidates against experimental murine leishmaniasis due to *Leishmania major*. Vaccine, 2004; 22:1631-9.
Akman L, Aksu HS, Wang RQ, Ozensoy S, Ozbel Y, Alkan Z, Ozcel MA, Culha G, Ozcan K, Uzun S, Memisoglu HR, Chang KP, Multi-site DNA polymorphism analyses of *Leishmania* isolates define their genotypes predicting clinical epidemiology of leishmaniasis in a specific region. J. Eukaryot Microbiol. 2000; 47:545-54.
Alexander J, Coombs GH, Mottram JC. *Leishmania mexicana* cysteine proteinase-deficient mutants have attenuated virulence for mice and potentiate a Th1 response. J Immunol. 1998; 161:6794-801.
Anderson WL, Shechter Y, Parikh I. Quantitation of methionyl peptides in nanomole quantities by a fluorometric method. Anal Biochem. 1978; 91:481-9.
Belkaid, Y., H. Jouin and G. Milon (1996). "A method to recover, enumerate and identify lymphomyeloid cells present in an inflammatory dermal site: a study in laboratory mice." J Immunol Methods 199(1): 5-25.
Belkaid Y, Kamhawi S, Modi G, Valenzuela J, Noben-Trauth N, Rowton E, Ribeiro J, Sacks DL. Development of a natural model of cutaneous leishmaniasis: powerful effects of vector saliva and saliva preexposure on the long-term outcome of *Leishmania major* infection in the mouse ear dermis. J Exp Med. 1998; 188:1941-53.
Bissonnette R, Tremblay JF, Juzenas P, Boushira M, Lui H. Systemic photodynamic therapy with aminolevullinic acid induces apoptosis in lesional T lymphocytes of psoriatic plaques. Journal of Investigative Dermatology. Jul. 2002;119(1):77-83.
Burchmore RJ, Rodriguez-Contreras D, McBride K, Merkel P, Barrett MP, Modi G, Sacks D, Landfear SM. Genetic characterization of glucose transporter function in *Leishmania mexicana*. Proc Natl Acad Sci U S A. 2003; 100:3901-6.
Campbell K, Diao H, Ji J, Soong L. DNA immunization with the gene encoding P4 nuclease of *Leishmania amazonensis* protects mice against cutaneous Leishmaniasis. Infect Immun. 2003; 71:6270-8.
Campbell K, Popov V, Soong L. Identification and molecular characterization of a gene encoding a protective *Leishmania amazonensis* Trp-Asp (WD) protein. Infect Immun. 2004; 72:2194-202.
Castro DJ, Saxton RE, Soudant J. The concept of laser phototherapy. Otolaryngolical Clinic of North America. Dec. 1996;29(6):1011-29.
Chang KP. Human cutaneous Leishmanias in a mouse macrophage line: propagation and isolation of intracellular parasites. Science. 1980; 209:1240-42.
Chang KP. Intracellular multiplication of *Leishmania donovani* during repeated passages in primary cultures of hamster peritoneal macrophages. J Parasitol. 1978; 64:931-3.
Chang KP, Akman L, Nielsen JS. Leishmania virulence and genetic heterogeneity. Clinical Dermatology. May-Jun. 1999;17(3):269-73.
Chang KP, Chang CS, Sassa S. Heme biosynthesis in bacterium-protozoon symbioses: enzymic defects in host hemoflagellates and complemental role of their intracellular symbiotes. Proc Natl Acad Sci U S A. 1975; 72:2979-83.
Chang.KP, Dwyer DM. Multiplication of a human parasite (*Leishmania donovani*) in phagolysosomes of hamster macrophages in vitro. Science. 1976; 193:678-80.
Chang KP, Hendricks DL. Laboratory cultivation and maintence of *Leishmania*.In: Human Parasite Diseases. vol. 1, Leishmaniasis (Chang K.-P. and Bray RS, eds). 1985; Elsevier, Amsterdam. pp. 213-246.

(Continued)

Primary Examiner—Scott D. Priebe
(74) *Attorney, Agent, or Firm*—Everest Intellectual Property Law Group; Tin-Chuen Yeung

(57) ABSTRACT

The present invention discloses the use of a mutant *Leishmania* as a suicidal vaccine wherein the mutant *Leishmania* is responsive to external signals to become porphyric and commit suicidal cytolysis. The mutant can be selected from natural *Leishmania* species or constructed by genetic engineering.

3 Claims, 23 Drawing Sheets
(2 of 23 Drawing Sheet(s) Filed in Color)

OTHER PUBLICATIONS

Chang KP, Reed SG, McGwire BS, Soong L. *Leishmania* model for microbial virulence: the relevance of parasite multiplication and pathoantigenicity. Acta Trop. 2003; 85:375-90.

Chang KP, Trager W. Nutritional significance of symbiotic bacteria in two species of hemoflagellates. Science. 1974; 183:531-2.

Chakrabarty R, Mukherjee S, Lu HG, McGwire BS, Chang KP, Basu MK. Kinetics of entry of virulent and avirulent strains of *Leishmania donovani* into macrophages: a possible role of virulence molecules (gp63 and LPG). Journal of Parasitology. Aug. 1996;82(4):632-5.

Chen DQ, Kolli BK, Yadava N, Lu HG, Gilman-Sachs A, Peterson DA, Chang KP. Episomal expression of specific sense and antisense mRNAs in *Leishmania amazonensis*: modulation of gp63 level in promastigotes and their infection of macrophages in vitro. Infect Immun. 2000; 68:80-6.

Chen DQ, Lu H, Chang KP. Replacement of *Leishmania* N-acetylglucosamine-1-phosphate transferase gene requires episomal rescue. Mol Biochem Parasitol. 1999; 100:223-7.

Chicharro C, Alvar J. Lower trypanosomatids in HIV/AIDS patients. Ann Trop Med Parasitol. 2003; 97 Suppl. 1:75-8.

Coler RN, Skeiky YA, Bernards K, Greeson K, Carter D, Cornellison CD, Modabber F, Campos-Neto A, Reed SG. Immunization with a polyprotein vaccine consisting of the T-Cell antigens thiol-specific antioxidant, *Leishmania major* stress-inducible protein I, and *Leishmania* elongation initiation factor protects against leishmaniasis. Infect Immun. 2002; 70:4215-25.

Cruz A, Coburn CM, Beverly SM. Double targeted gene replacement for creating null mutants. Proc Natl Sci U S A. 1991; 88:7170-4.

Du Y, Maslov DA, Chang KP. Monophyletic origin of beta-division proteobacterial endosymbionts and their coevolution with insect trypanosomatid protozoa Blastocrithidia culicis and Crithidia spp. Proceedings of the National Academy of Science U S A. Aug. 30, 1994;91(18):8 437-41.

Edgeworth RL, San JH, Rosenzweig JA, Nguyen NL, Boyer JD, Ugen KE. Vaccine development against HIV-1: current perspectives and future directions. Immunology Res. 2002;25(1):53-74.

Etges R, Muller I. Progressive disease or protective immunity to *Leishmania major* infection: the result of a network of stimulatory and inhibitory interactions. J Mol Med. 1998; 76:372-90.

Freedman DJ, Beverly SM. Two more independent selectable markers for stable transfection of *Leishmania*. Mol Biochem Parasitol. 1993; 62:37-44

Friesen SA, Hjortland GO, Madsen SJ, Hirschberg H, Engebraten O, Nesland JM, Peng Q. 5-Aminolevulinic acid-based photodynamic detection and therapy of brain tumors (Review). International Journal of Oncology. Sep. 2002;21(3):577-82.

Gibson SL, Havens JJ, Nguyen ML, Hilf R. Delta-aminolaevulinic acid-induced photodynamic therapy inhibits photoporphyrin IX biosynthesis and reduces subsequent treatment efficacy in vitro. British Journal of Cancer. Jun. 1999;80(7):998-1004.

Glerum DM, Shtanko A, Tzagoloff A, Gorman N, Sinclair PR. Cloning and identification of HEM14, the yeast gene for mitochondrial protoporphyrinogen oxidase. Yeast. Nov. 1996;12(14):1421-5.

Gourley DG, Schuttelkopf AW, Leonard GA, Luba J, Hardy LW, Beverly SM, Hunter WN. Pteridine reductase correlates pterin metabolism with drug resistance intrypanosomatid parasites. National Structure Biology. Jun. 2001;8(6):521-5.

Goyard S, Beverley SM. Blasticidin resistance: a new independent marker for stable transfection of *Leishmania*. Mol Biochem Parasitol. 2000; 108:249-52.

Gramiccia M, Gradoni L, Troiani M. HIV-*Leishmania* co-infections in Italy. Isoenzyme characterization of *Leishmania* causing visceral leishmaniasis in HIV patients. Trans R Soc Trop Med Hyg. 1992; 86:161-3.

Gumy A, Louis JA, Launois P. The murine model of infection with *Leishmania major* and its importance for the deciphering of mechanisms underlying differences in Th cell differentiation in mice from different genetic backgrounds. Int J Parasitol. 2004; 34:433-44.

Harth Y, Hirshowitz B, Kaplan B. Modified topical photodynamic therapy of superficial skin tumors utilizing aminolevulinic acid, penetration enhancers, red light, and hyperthermia. Dermatol Surg. 1998; 24:723-6.

Hodgkinson VH, Soong L, Duboise SM, McMahon-Pratt D. *Leishmania amazonensis*: cultivation and characterization of Axenic amastigote-like organisms. Exp Parasitol. 1996; 83:94-105.

Houde M, Bertholet S, Gagnon E, Brunet S, Goyette G, Laplante A, Princiotta MF, Thibault P, Sacks D, Desjardins M. Phagosomes are component organelles for antigen cross-presentation. Nature. 2003; 425:402-6.

Ilg T, Demar M, Harbecke D. Phosphoglycan repeat-deficient *Leishmania mexicana* parasites remain infectious to macrophages and mice. J Biol Chem. 2001; 276:4988-97.

Joshi PB, Webb JR, Davies JE, McMaster WR. The gene encoding streptothricin acetyltransferase (sat) as a selectable marker for *Leishmania* expression vectors. Gene. 1995; 156:145-9.

Kamhawi S, Belkaid Y, Modi G, Rowton E, Sacks D. Protection against cutaneous leishmaniasis resulting from bites of uninfected sand flies. Science. 2000; 290:1351-4.

Kappas A, Song CS, Sassa S, Levere RD, Granick S. The occurrence of substances in human plasma capable of inducing the enzyme delta-aminolevulinate synthetase in liver cells. Proc Natl Acad Sci U S A. 1969; 64:557-64.

Kawazu S, Lu HG, Chang KP. Stage-independent splicing of transcripts two heterogeneous neighboring genes in *Leishmania amazonensis*. Gene. 1997; 196:49-59.

Kaye PM, Coburn C, McCrossan M, Beverly SM. Antigens targeted to the *Leishmania* phagolysome are processed for CD4+ T cell recognition. European Journal of Immunology. Sep. 1993;23(9):2311-9.

Kurlandzka A, Zoladek T, Rytka J, Labbe-Bois R. The alternative pathway of haem synthesis via dehydroisocoproporhyrinogen in mutants of *Saccharomyces cervisiae* partially deficient in uroporphyrinogen decarboxylase activity. Biochemistry Journal. Jan. 1, 1991;273(Pt 1):246-7.

Lane N. New light on medicine. Scientific American. Jan. 2003; pp. 38-45.

LeBowitz JH, Cruz A, Beverly SM. Thymidine kinase as a negative selectable marker in *Leishmania major*. Molecular Biochemistry Parasitology. Apr. 1992;51(2):321-5.

LeBowitz JH, Coburn CM, McMahon-Pratt D, Beverley SM. Development of a stable *Leishmania* expression vector and application to the study of parasite surface antigen genes. Proceedings of the National Academy of Science U S A. Dec. 1990;87(24):9736-40.

Liu X, Chang KP. The 63-kilobase circular amplicon of tunicamycin-resistant *Leishmania amazonensis* contains a functional N-acetylglucosamine-1-phosphate transferase gene that can be used as a dominant selectable marker in transfection. Mol Cell Biol. 1992; 12:4112-22.

Lipoldova M, Svobodova M, Havelkova H, Krulova M, Badalova J, Nohynkova E, Hart AA, Schlegel D, Volf P, Demant P. Mouse genetic model for clinical and immunological heterogeneity of leishmaniasis. Immunogenetics. 2002; 54:174-83.

Locksley RM, Heinzel FP, Sadick MD, Holaday BJ, Gardner KD Jr. Murine cutaneous leishmaniasis: susceptibility correlates with differential expansion of helper T-cell subsets. Ann Inst Pasteur Immunol. 1987; 138:744-9.

Melby PC, Chandrasekar B, Zhao W, Coe JE. The hamster as a model of human visceral leishmaniasis: progressive disease and impaired generation of nitric oxide in the face of a prominent Th1-like cytokine response. J Immunol. 2001; 166:1912-20.

Mollenkopf H, Dietrich G, Kaufmann SH. Intracellular bacteria as targets and carriers for vaccination. Biological Chemistry. Apr. 2001;382(4):521-32.

Morris RV, Shoemaker CB, David JR, Lanzaro GC, Titus RG. Sandfly maxadilan exacerbates infection with *Leishmania major* and vaccinating against it protects against *L. major* infection. J Immunol. 2001; 167:5226-30.

Nadim A, Javadian E, and Mohebali M. The experience of leishmanization in the Islamic Republic of Iran. La Revue de Sante de la Mediterranee orientale. 1997; 3:284-89.

Olobo JO, Gicheru MM, Anjili CO. The African green monkey model for cutaneous and visceral leishmaniasis. Trends Parasitol. 2001; 17:588-92.

Pacheco RS, Ferreira MS, Machado MI, Brito CM, Pires MQ, Da-Cruz AM, Coutinho SG. Chagas'disease and HIV co-infection: genotypic characterization of the *Trypanosoma cruzi* strain. Mem Inst Oswaldo Cruz. 1998; 93:165-9.

Papadopoulou B, Roy G, Breton M, Kundig C, Dumas C, Fillion I, Singh AK, Olivier M, Ouellette M. Reduced infectivity of a *Leishmania donovani* biopterin transporter genetic mutant and its use as an attenuated strain for vaccination. Infections and Immunology. Jan. 2002;70(1):62-8.

Peng Q, Warloe T, Berg K, Moan J, Kongshaug M, Giercksky KE, Nesland JM. 5-Aminolevulinic acid-based photodynamic therapy. Clinical research and future challenges. Cancer. Jun. 15, 1997;79(12):2282-308.

Probst RJ, Wellde BT, Lawyer PG, Stiteler JS, Rowton ED. Rhesus monkey model for *Leishmania major* transmitted by *Phlebotomus papatasi* sandfly bites. Med Vet Entomol. 2001; 15:12-21.

Reed SG. Leishmaniasis vaccination: targeting the source of infection. J Exp Med. 2001; 194:F7-F9.

Requena JM, Soto M, Doria MD, Alonso C. Immune and clinical parameters associated with *Leishmania infantum* infection in the golden hamster model. Vet Immunol Immunopathol. 2000; 76:269-81.

Rozental S, de Carvalho TU, de Souza W. Influence of the endosymbiont on the interaction of *Crithidia deanei* with macrophages. Microsc Electron Biol Cel. 1987; 11:167-79.

Sah JF, Ito H, Kolli BK, Peterson DA, Sassa S, Chang KP. Genetic rescue of *Leishmania* deficiency in porphyrin biosynthesis creates mutants suitable for analysis of cellular events in uroporphyria and for photodynamic therapy. J Biol Chem. 2002; 277:14902-9.

Sassa S. Delta-aminolevullinic acid dehydratase assay. Enzyme. 1982; 28:133-45.

Sassa S. Hematologic aspects of the porphyrias. International Journal of Hematology. Jan. 2000;71(1):1-17.

Sassa S, Granick S, Bickers DR, Bradflow HL, Kappas A. A microassay for uroporphyrinogen I synthase, one of three abnormal enzyme activities in acute intermittent porphyria, and its application to the study of the genetics of this disease. Proc Natl Acad Sci U S A. 1974; 71:732-6.

Sassa S, Nagai T. The role of heme in gene expression. International Journal of Hematology. Apr. 1996;63(3):167-78.

Scott P, Natovitz P, Coffman RL, Pearce E, Sher A. Immunoregulation of cutaneous leishmaniasis. T cell lines that transfer protective immunity or exacerbation belong to different T helper subsets and respond to distinct parasite antigens. J Exp Med. 1988; 168:1675-84.

Shaw JJ. Taxonomy of the genus *Leishmania*: present and future trends and their implications. Mem Inst Oswaldo Cruz. 1994; 89:471-8.

Somanna A, Mundodi V, Gedamu L. Functional analysis of cathepsin B-like cysteine proteases from *Leishmania donovani* complex. Evidence for the activation of latent transforming growth factor beta. J Biol Chem. 2002; 277:25305-12.

Spath GF, Garraway LA, Turco SJ, Beverley SM. The role(s) of lipophosphoglycan (LPG) in the establishment of *Leishmania major* infections in mammalian hosts. Proc Natl Acad Sci U S A. 2003; 100:9536-41.

Spath GF, Lye LF, Segawa H, Sacks DL, Turco SJ, Beverley SM. Persistence without pathology in phosphoglycan-deficient *Leishmania major*. Science. 2003; 301:1241-3.

Spath GF, Lye LF, Segawa H, Turco SJ, Beverley SM. Identification of a compensatory mutant (lpg2-REV) of *Leishmania major* able to survive as amastigotes within macrophages without LPG2-dependent glycoconjugates and its significance to virulence and immunization strategies. Infect Immun. 2004; 72:3622-7.

Spikes JD, Bommer JC. Photosensitizing properties of mono-L-aspartyl chlorin e6 (NPe6): a candidate sensitizer for the photodynamic therapy of tumors. Journal of Photochemistry and Photobiology B. Feb. 1993;17(2):135-43.

Strelkova MV. Susceptibility to and the characterisitics of the course of experimental leishmaniasis in different species of mammals infected with *Leishmania major*, *L. turanica* and *L. gerbilli* Medarazitol (Mosk). 1991; (1):35-9.

Tamar S, Dumas C, Papadopoulou B. Chromosome structure and sequence organization between pathogenic and non-pathogenic *Leishmania spp*. Mol Biochem Parasitol. 2000; 111:401-14.

Taylor EL, Brown SB. The advantage of aminolevulinic acid photodynamic therapy in dermatology. Journal of Dermatological Treatment. 2002;13 Suppl 1:S3-11.

Tetaud E, Lecuix I, Sheldrake T, Baltz T, Fairlamb AH. A new expression vector for *Crithidia fasciculata* and Leishmania. Molecular Biochemistry and Parasitology. Apr. 9, 2002;120(2):195-204.

Titus RG, Gueiros-Filho FJ, de Freitas LA, Beverley SM. Development of a safe live *Leishmania* vaccine line by gene replacement. Proc Natl Acad Sci U S A. 1995; 92:10267-71.

Valenzuela JG, Belkaid Y, Garfield MK, Medaz S. Kamhawi S, Rowton ED, Sacks DL, Ribeiro JM. Toward a defined anti-*Leishmania* vaccine targeting vector antigens: characterization of a protective salivary protein. J Exp Med. 2001; 194:331-42.

Wainwright M. Photodynamic antimicrobial chemotherapy (PACT). Journal of Antimicrobial Chemother. Jul 1998;42(1):13-28.

Wang W, Boynton JE, Gillham NW. Genetic control of chlorophyll biosynthesis in chlamydomonas: analysis of a mutant affecting synthesis of delta-aminolevulinic acid. Cell. Sep. 1975;6(1):75-84.

Zhang K, Showalter M, Revollo J, Hsu FF, Turk J, Beverley SM. Sphingolipids are essential for differentiation by not growth in *Leishmania*. EMBO J. 2003; 22:6016-26.

* cited by examiner

FIG. 1: Summary of enzymatic pathways in the biosynthesis of heme

FIG. 3
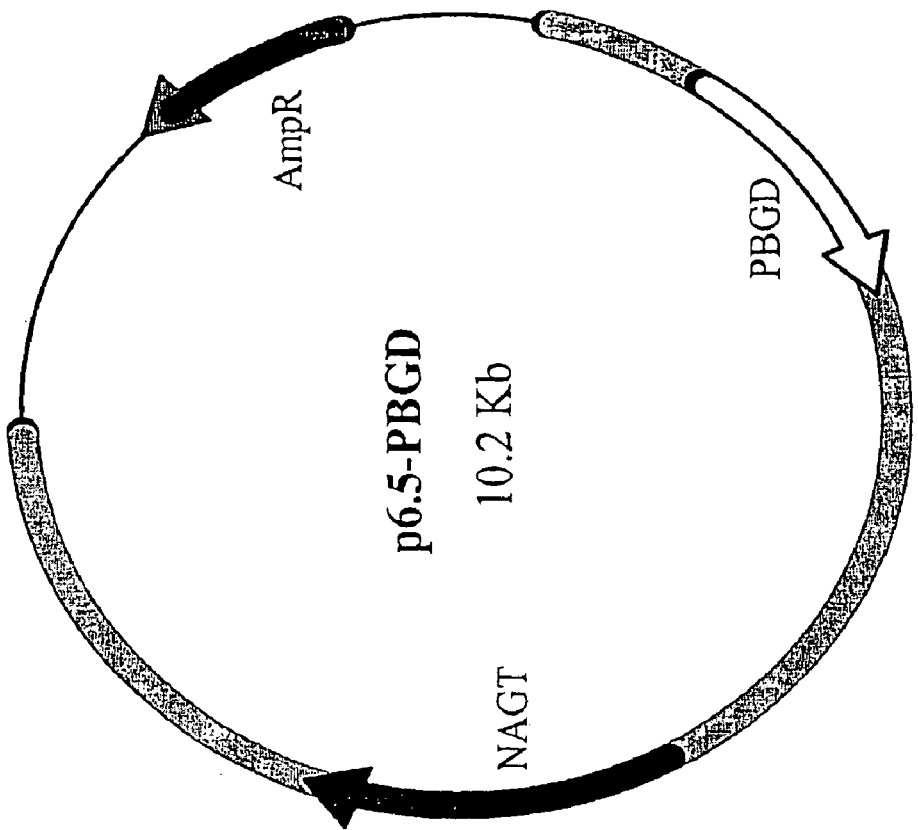
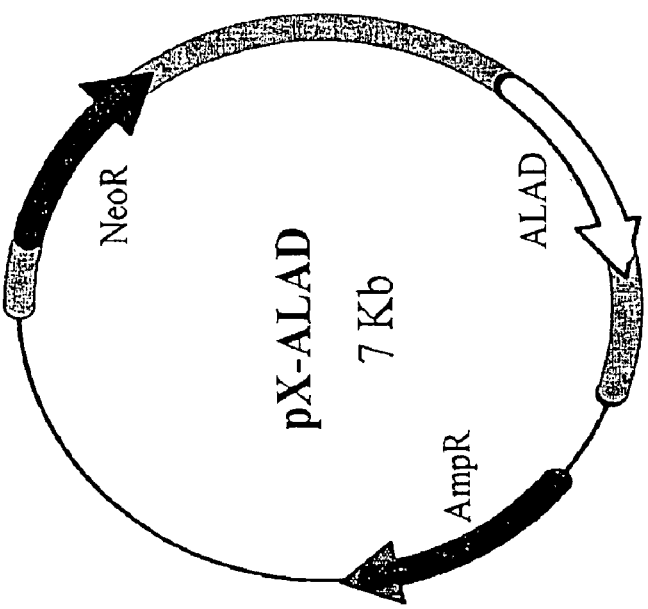

FIG. 4
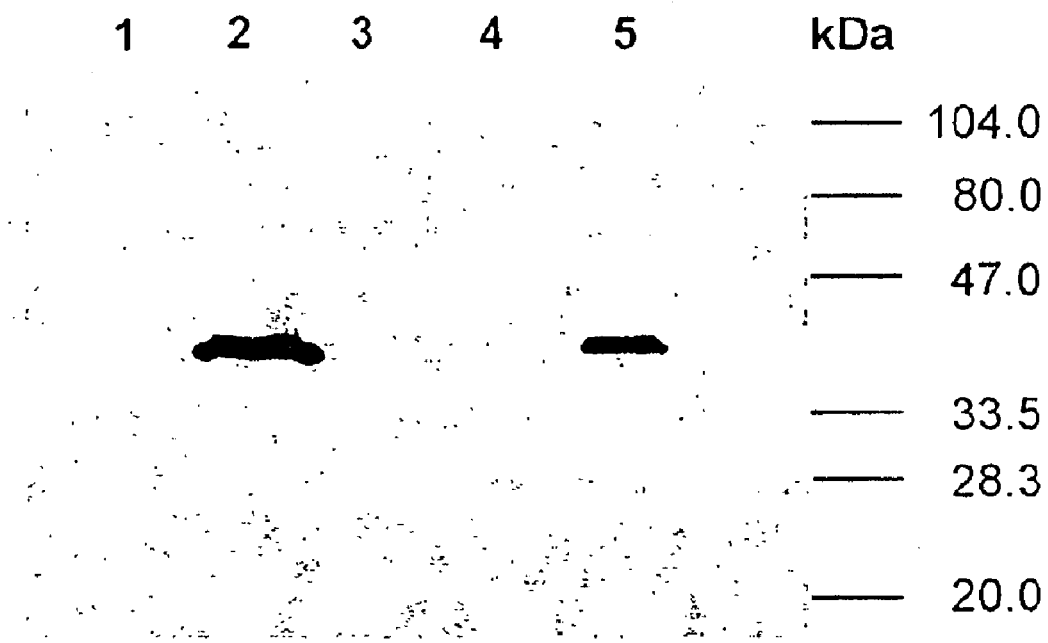
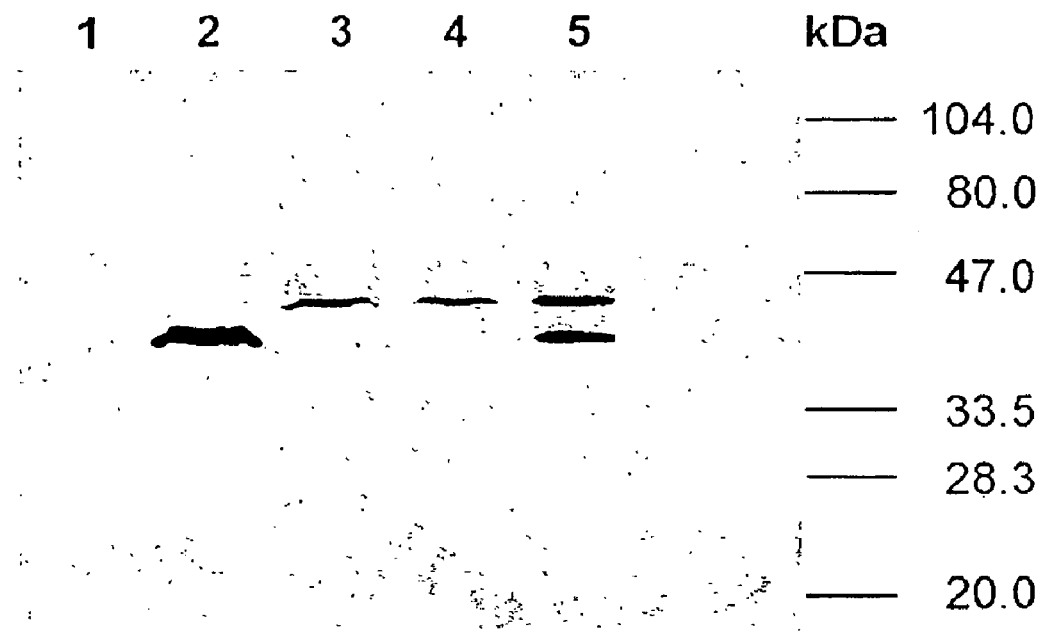

Trypanpsome incomplete heme biosynthesis pathway

FIG. 11

Porphyria of transgenic *Leishmania* inducible with exogenous ALA

| Extracellular | Cytosol | Mitochondria |

ALA (Inducing signal) → ALA
↓ ALAD 2
PBG
↓ PBGD 3
HMB
↓
URO' I
↓ UROD 5
COPRO' I ┈┈→

FIG. 17
AJ mice 48 days post vaccination
Porphyric 2 transfect
Porphyric 2 transfect
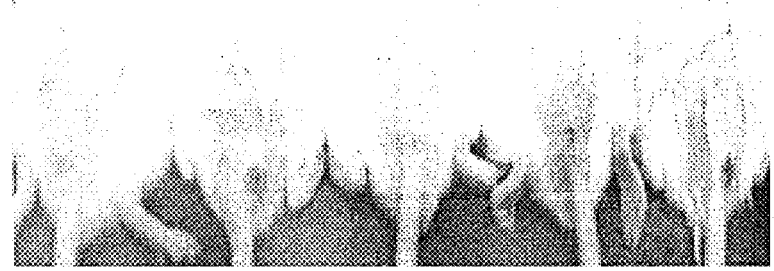
Aporphyric 1 transfect

FIG. 18

Experimental visceral leishmaniasis

FIG. 22
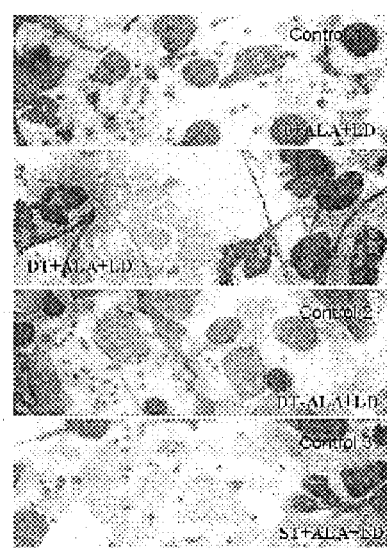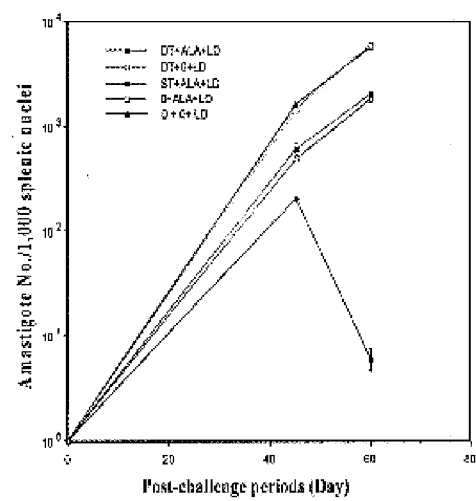

SUICIDAL MUTANT *LEISHMANIA* VACCINE

TECHNICAL FIELD

The present invention discloses the use of a mutant *Leishmania* as a suicidal vaccine wherein the mutant *Leishmania* is responsive to external signals to become porphyric and commit suicidal cytolysis. The mutant can be selected from natural *Leishmania* species or constructed by genetic engineering.

REFERENCE TO SEQUENCE LISTING

A sequence listing is included as a part of this disclosure and all information contained therein is incorporated herein by reference.

BACKGROUND OF THE INVENTION

The present invention discloses the use of a mutant *Leishmania* as a suicidal vaccine wherein the mutant *Leishmania* is responsive to external signals to become porphyric and commit suicidal cytolysis.

*Leishmania* spp. are flagellated trypanosomatid protozoa commonly known as trypanosomes. Essentially all of them are parasites, of which overwhelming majority are non-pathogenic to humans, but live in other animals and sometimes in plants. However, certain species of *Leishmania* are pathogenic to their hosts, resulting in leishmaniasis. The best known pathogenic species are vector-borne *Trypanosoma* spp., which cause African Sleeping Sickness as extracellular parasites in body fluids and South American Chagas disease as parasites with both extracellular and intracellular phases. Recently, *Leishmania* spp. have attracted attention for causing "Baghdad boils" via sand fly bites among soldiers sent to Iraq and Afghanistan.

*Leishmania* spp. are uniquely suitable among trypanosomes to serve as a live vaccine model for the following reasons:

First, *Leishmania* spp. naturally infect antigen-presenting cells (APC), i.e., dendritic cells and macrophages, hence inherently suitable for homing vaccines to a desired destination. *Leishmania* not only infect macrophages but utilize them as their exclusive host cells by residing in their phagolysosomes (Chang and Dwyer, 1976). This is the very site where antigens/vaccines are processed for presentation via the lysosomal major histocompatibility complex (MHC) Class II pathway and also via the cytosolic MHC Class I pathway by cross-presentation (Houde et al. 2003). This APC-homing ability of *Leishmania* makes them exceptionally attractive for consideration as a live vaccine model. Micro-organisms, which share with *Leishmania* this specific feature, are very few and limited to pathogenic bacteria, e.g., *Coxiella burnetii*, *Legionella pneumophilia* and *Mycobacterium leprae*. Unlike these microbes, *Leishmania* have a number of advantages as single-cell eukaryotes.

Second, *Leishmania* spp. are amenable to laboratory maintenance in culture and in animal models. They grow in vitro as flagellated motile "promastigotes", which normally live as extracellular parasites in the gut of blood sucking sand flies. Continuous cultivation of promastigotes is readily achievable for most species by using tissue culture media commercially available for mammalian and insect cells (Chang and Hendricks, 1985). These promastigotes differentiate into infective or "metacyclic" forms in fly gut or as they reach stationary phase in culture. They further differentiate into non-motile "amastigotes"—the intra-macrophage stage normally found in the mammalian hosts. Some species, especially *L. amazonensis* and *L. mexicana*, grow readily and continuously free of macrophages as "axenic amastigotes" under suitable conditions at acidic pH and mammalian body temperature (Hodgkinson et al., 1996). These species also grow continuously as intracellular amastigotes in macrophage cell lines, e.g., J774 series (Chang, 1980; Chang, 1978; Chang and Hendricks, 1985). These and other species can be further passaged cutaneously or viscerally in rodents, e.g., hamsters and mice (Chang and Hendricks, 1985).

Third, non-pathogenic *Leishmania* spp. exist, originating from lizards, e.g., *L. tarentolae* and from rodents, e.g., *L. enriettii* of guinea pig and *L. turanica* of the great gerbil in Gobi desert. There is documented evidence for these species to produce no disease in human volunteers at least for *L. gerbilli* (Strelkova, 1991), despite it is phylogenetically closely related to *L. major* (FIG. 1). *L. major* is well-known to cause self-healing simple cutaneous leishmaniasis (CL). This is the least pathogenic one among 2 dozens or so additional species of known human pathogens in both *Leishmania* and *Viannia* subgenus (Shaw, 1994). Some of them cause not only CL but also facial disfiguring mucocutaneous leishmaniasis (MCL), e.g., *L. braziliensis* and *L. panamensis* or the potentially fatal visceral leishmaniasis (VL), e.g., the Indian kala-azar caused by *L. donovani* and the Mediterranean infantile VL (IVL) caused by *L. infantum*. Included for the present invention are well-established laboratory species as well as field isolates appropriately genotyped (see legend to FIG. 1), ranging from totally non-pathogenic to highly virulent species.

Fourth, human populations have been successfully vaccinated against cutaneous leishmaniasis with lesion-derived live amastigotes of *L. major*. This is known as a time-honored procedure of "Leishmanization" (i.e., vaccination of children with virulent parasites from diseased patients). It has been practiced for centuries and proven effective to elicit life-long protective immunity against CL in the Middle East and Central Asia. Iranian and Russian workers have documented this more scientifically. From 1978 to 1989, Mohebali et al. had "leishmanized" or vaccinated about 2 million individuals in their upper arms with a live *L. major* culture originally from a Great Gerbil in Iran. This "vaccination" confers protective immunity in >90% of the leishmanized individuals, but the procedure takes 10-15 months, during which period "vaccinees" develop full-blown lesions followed by spontaneous healing, just like the natural infection (Nadim et al., 1997). In addition, non-healing lesions occurred in 1-2/10,000 cases. Similar results were reported in Central Asia using a different strain of live *L. major* by Dr. Leonid Krasnonos et al. in Isaev Institute of Medical Parasitology, Samakan, Uzbekistan. Thus, "Leishmanization" has a proven track record of effectiveness in contrast to the uncertain benefits of BCG vaccination for tuberculosis. *Leishmania* also compare favorably over BCG to serve as potential vehicles to deliver add-on vaccines, since these and other related trypanosomes are readily cultivable and since they are genetically efficient and versatile to express foreign genes. One principal disadvantage common to all live vaccine models is the issue of residual pathogenicity, as described for "Leishmanization". An important aspect of the present disclosure is to address this issue by using transgenic *Leishmania* responsive to external signals to commit suicidal cytolysis.

Fifth, there is a substantial body of information available for the immune response of animals to *Leishmania* infection. Experimental leishmaniasis has been extensively used for elucidating rodent immunogenetics and immunobiology, especially the BALB/c mouse-*L. major* model (Gumy et al., 2004). The use of this model has indeed led to the significant discovery in the dichotomy of animal immune response via Th1 and Th2 pathways (Locksley et al., 1987; Scott et al., 1988). The regulation of these pathways in relation to protective immunity is still under intensive investigation (Etges and Muller, 1998), including the use of different *Leishmania*-mouse combinations (Lipoldova et al., 2002). There have been additional efforts to extend such investigation to hamster and primate models (Melby et al., 2001; Olobo et al., 2001; Probst et al., 2001; Requena et al., 2000). This wealth of knowledge has proven its value in current efforts to develop *Leishmania* DNA-based and recombinant peptide vaccines as well as using sand fly saliva antigens (Ahmed et al., 2004; Belkaid et al., 1996; Belkaid et al. 1998; Campbell et al., 2003; Campbell et al., 2004; Coler et al., 2002; Kamhawi et al., 2000; Morris et al.,; 2001; Reed, 2001; Valenzuela et al., 2001).

Sixth, *Leishmania* spp. are amenable to genetic manipulations for expressing endogenous or foreign genes via transfection by electroporation. The genome project has been essentially completed for *L. major*. This and other species possess all the necessary machineries of eukaryotic types not only for gene replication, mRNA transcription and protein translation but also for post-translational modifications of proteins. The last cellular events, which may have some importance in vaccine presentation, are absent in bacterium-based live vaccine models, e.g., *Salmonella* and BCG. There are at least 6 different markers available for selection of transfectants in conjunction with the use of *Leishmania-E. coli* shuttle vectors. The principal is the pX series (Freedman and Beverley, 1993; Goyard and Beverley, 2000). In addition, we have developed p6.5 using *Leishmania* endogenous N-acetylglucosamine-1-phosphate transferase gene (nagt) as a selectable marker for tunicamycin (TM)-resistance (Chen et al., 2000, Kawazu et al., 1997; Liu and Chang, 1992; Sah et al., 2002; Somanna et al., 2002). There have been numerous reports of *Leishmania* gene knock-outs and knock-ins by homologous recombination (Alexander et al., 1998; Burchmore et al., 2003; Ilg et al., 2001; Cruz et al., 1991; Spath et al., 2003, 2004; Zhang et al., 2003). Such genetic manipulations have been routinely carried out by us (Chen et al., 2000; Chen et al., 1999; Sah et al., 2002) and will be used for the proposed studies.

Seventh, vaccination of animals by genetically modified *Leishmania* has produced favorable outcome. Mice were protected against infection by *L. major* or *L. mexicana* when immunized with their respective knockouts of house-keeping genes, e.g., dhfr (Titus et al., 1995) or virulence genes, i.e., lpg 1, lpg2 and cysp (Alexander et al., 1998; Ilg et al., 2001; Spath et al., 2003, 2004).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is an example of constructs of mammalian genes encoding porphobilinogen deaminase (PBGD) and δ-aminolevulinate dehydratase (ALAD) in p6.5 and pX vectors specific for transfection of *Leishmania*, respectively;

FIG. 4 shows Western blot analysis of *Leishmania amazonensis* transfectants expressing δ-aminolevulinate dehydratase and porphobilinogen deaminase;

FIG. 11 is a schematic diagram showing the porphyria of transgenic *Leishmania* inducible with exogenous ALA;

FIG. 17 shows ALA-mediated suppression of lesion development by transgenic *L. amazonensis* in the mouse tailbase model. Mice each inoculated at the tailbase $10^7$ alad/pbgd double transfectants (upper 2 rows) or pbgd single transfectants (last row)/100 ul PBS, treated daily with 100 ul 100 mM ALA 4 times and exposed to illumination via wrap-around-the-cage red transparent paper daily at regular periodicity for 4 days;

FIG. 18 shows Vervet or African green monkey infected with non-porphyric and porphyric *L. amazonensis*. Single pbgd and double alad/pbgd transfectants grown under non-selective conditions for 5 days to stationary phase and diluted 10-fold in maintenance solution, i.e., HBSS-HEPES (pH 7.4) plus 0.01% BSA, for shipping. Upon arrival, cells in all cultures were sedimented and resuspended in the maintenance solution to a density of $10^8$ cells/ml. Aliquots of single and double transfectants were treated with 1 mM ALA in the dark for 3 days. Only ALA-treated double transfectants developed uroporphyria. Groups of 5 vervet monkeys each were inoculated on shaved right eye-brow ridge with $10^7$ cells/animal using the following cells: [1] double transfectants with ALA (porphyric); [2] double transfectants without ALA (non-porphyric control); and [3] single transfectants with ALA (another non-porphyric control group). All caged monkeys were exposed daily for 6 days at normal lighting periodicity to red light source (50 watt), which was placed above the cage. Representative photos taken 16 days after inoculation of monkeys with porphyric *Leishmania* (#14) versus with non-porphyric (#10);

FIG. 19 shows the prevention of weight loss/cachexia of hamsters (0+0+LD) in experimental Kala-azar by "Vaccination" with *Leishmania amazonensis* porphyric suicidal mutants (DT+ALA+LD);

FIG. 20 shows splenic amastigotes abundant in unvaccinated control (Upper Panel 0+0+LD), those vaccinated with non-porphyric group (Middle DT+0+LD) and virtually absent in vaccinated porphyric group (Lower). Challenged with *Leishmania donovani* DD8 intracardially at $10^7$ amastigotes/hamster 14 day post-vaccination (Giemsa-stain 47 days post challenge);

FIG. 21 shows the "Vaccination" of hamsters with *Leishmania amazonensis* porphyric suicidal mutants prevents weight loss (Left) and splenomegaly (right) after *L. donovani* challenges. The values for body weights were from all animals available at specific time points. Two animals were sacrificed per group per time point for assessing spleen weights and parasite loads;

FIG. 22 shows the "Vaccination" of hamsters with pophyric *Leishmania amazonensis* suicidal mutants reduces splenic parasite loads after *Leishmania donovani* challenging. Impression smears (Left panel) of cut spleens were Geimsa-stained and examined microscopically under oil immersion lens to enumerate amastigotes per 1,000 splenic nuclei as a measure of parasite loads (Right Panel). Note: Parasite loads decrease precipitously after day 45 in contrast to the control groups. The data are consistent with the data for animal body weights and spleen weights; and FIG. 23 shows the *Leishmania* antigen- and mitogen-specific proliferation of Lymphocytes from experimental and control groups. Lymph nodes of hamsters from experimental and control groups, as indicated, were used 45 days after challenging infection to prepare mononuclear cell-suspension ($10^6$/ml). Aliqouts of 100 ul were cultured in 96 well flat bottom tissue culture plates (Nunc, Denmark). 100 ul of Conconavalin A or soluble *L. donovani* promastigote antigens were added to each well, giving a final concentration of 10 ug/ml and 20 ug/ml, respectively. Cultures were prepared in triplicate for each sample and incubated at 37° C. and 5% $CO_2$ for 3 days and 5 days for Con-A treated and antigen-treated cells, respectively. Eighteen hours prior to termination of incubation of cultures, 0.5 uCi of tritiated-thymidine was added to each well. Cells were harvested on to glass fiber mats (Whatman) for liquid scintillation counting.

DETAILED DESCRIPTION OF THE INVENTION

While this invention is susceptible to embodiments in many different forms, it is shown in the drawings and will herein be described in detail a preferred embodiment of the invention with the understanding that the present disclosure is to be considered as an exemplification of the principles of the invention and is not intended to limit the broad aspect of the invention to the embodiments illustrated.

The present invention discloses the use of a mutant *Leishmania* as a suicidal vaccine wherein the mutant *Leishmania* is responsive to external signals to become porphyric and commit suicidal cytolysis. We exploit the virtual absence of heme biosynthesis pathway in trypanosomes to identify or construct their genetic mutants for time-controllable induction of an intense and sustained porphyric state, making it possible to consider their use for targeted release of antigens from the *Leishmania.*

Porphyrins are metabolic intermediates in the biosynthesis pathway of heme as shown in FIG. 2 (Sassa and Nagai 1996). Heme is an indispensable component required for respiration to produce energy in all aerobic organisms, including humans. All porphyrin intermediates formed in this pathway, i.e., uroporphrynogen I, uroporphyrinogen III, coproporphyrinogen III, protoporphyrinogen IX, and protoporphyrin IX are also inherently cytotoxic, especially on exposure to UV irradiation. This results in the generation of free radicals due to photosensitivity of porphyrins. Abnormal accumulation of porphyrins has been reported to result from a dysfunctional heme biosynthesis pathway, leading to human diseases known as "porphyria." (Sassa 2000). Porphyric individuals suffer from photophobia, tissue necrosis, organ failure and other related systemic disorders. There are different forms of human porphyria, caused by the accumulation of different porphyrin species, resulting from genetic defects of different porphyrin metabolizing enzyme as well as their inhibition by environmental poisons, such as lead.

Application of porphyrins or their precursor, delta-aminolevulinate (ALA) alone is considered to have therapeutic potentials against microbial infection and tumors, especially when this is followed by UV irradiation (Wainwright 1998;

Figure 1:
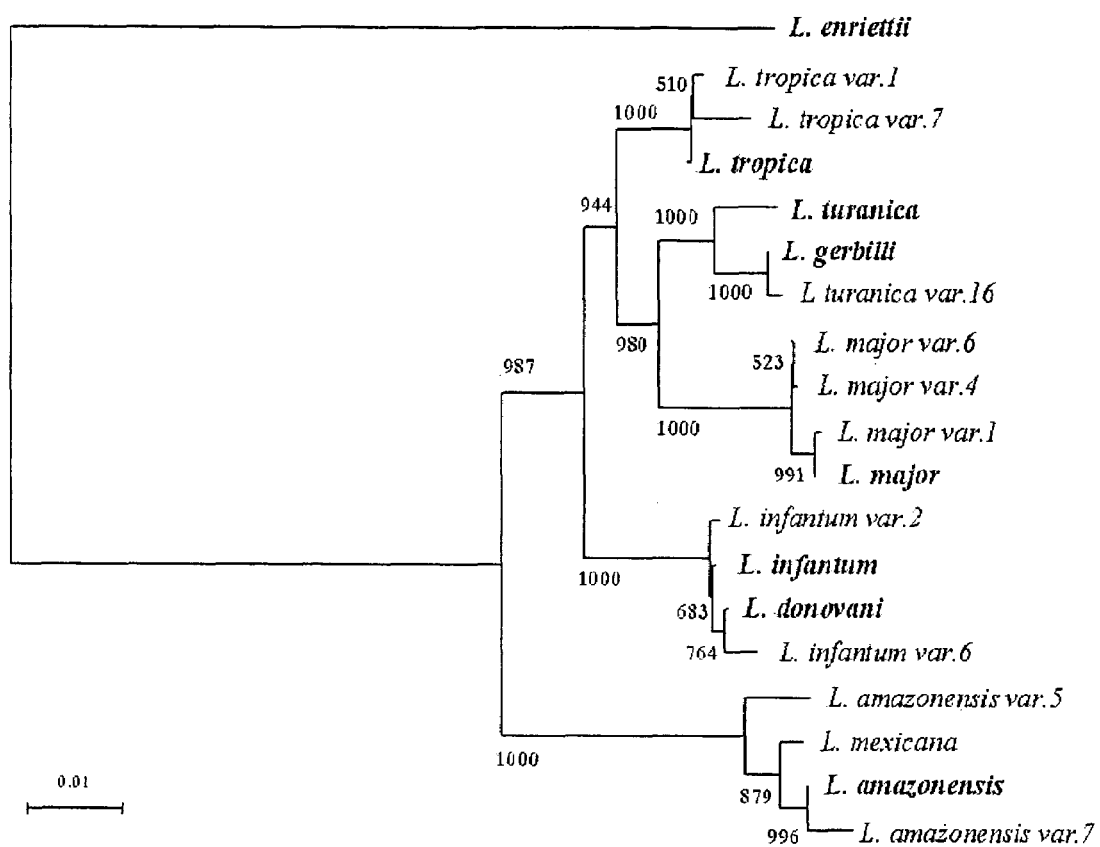
FIG. 1 is a schematic diagram showing the nineteen *Leishmania* genotypes and their phylogenetic relationship based on analysis of about 50 nagt sequences from approximately 150 independent isolates. 1401 bp N-acetylglucosamine-1-phosphate transferase gene (nagi) PCR-amplified from genomic DNAs as a single band (Akman et al., 2000). Phylogenic tree constructed from 1330 bp of the approximately 1.4 kb sequences with Clustal X (neighbor joining method with 1000 bootstrap trials). Vars. 1-16 denote variants with nucleotide substitutions, as indicated by the numbers shown, against a randomly selected type species within individual clades of *L. tropica, L. major/L. turanica, L. infantum/donovani* and *L. amazonensis*. Topology of the trees remains essentially identical when the same database was analyzed by using other programs based on different algorithms. This has been further verified by analysis of a different database from another equally conserved gene encoding a putative ferrochelatase.

Friesen et al. 2002). These procedures have been shown to kill certain pathogenic microorganisms and, more recently, tumor cells in "photodynamic therapy." In the latter cases, porphyrins are either administered exogenously or induced endogenously within the tumor cells using ALA, the product of ALA-synthase (ALAS)—the first of the eight enzymes in the heme biosynthesis pathway of mammals. The porphyric state generated by either way is non-targeted and transient, and the level of porphyrin accumulation is relatively low. This is due to the substrate "flow-through" and/or feedback and allosteric inhibition in the presence of a complete heme biosynthesis pathway in all aerobic organisms.

The present invention exploits the virtual absence of heme biosynthesis pathway in trypanosomes to identify or construct their genetic mutants for time-controllable induction of an intense and sustained porphyric state, making it possible to consider their use for targeted release of antigens from the Leishmania to immunize the host cell from subsequent Leishmania infection. This is the unique aspect of the present invention.

There has been no similar concept and methodology developed previously with this group of organisms for such applications. The closest materials generated previously are suicidal mutants of Leishmania, but they were constructed not with genes in the heme pathway, but by negative selections for virulence gene knockouts (Titus et al. 1995; Alexander et al. 1998; Gourley et al. 2001; Papadopoulou et al. 2002) or by reverse genetics using widely publicized schemes, e.g., transfection with thymidine kinase gene for responsiveness to ganciclovir as the trigger (LeBowitz et al 1992). These suicidal mutants also incorporate no time-controllable elements, as designed in the present invention. U.S. patent application Ser. No. 10/293,867 to Chang et al. discloses using this mutant suicidal Leishmania for delivery of a transgene product to targeted mammalian cells. However, the use of the mutant Leishmania as a live vaccine against Leishmania infections was not disclosed by Chang et al.

Other materials peripherally related to the constructs of the present invention are knockout mutants of individual genes encoding porphyrin metabolizing enzymes in single cell organisms, e.g., algae, yeasts (Kurlandzka et al. 1991; Glerum et al. 1996) and Chlamydomonas (Wang et al. 1975). These mutants have been used for isolation of specific porphyrin species, but have not been considered for use as vaccines. Remotely relevant are single experimental steps used in photodynamic therapy of tumors, i.e., ALA induction of these cells to develop a transient porphyric state (Abels et al. 1997; Gibson et al. 1999) and direct administration of porphyrins (Afonso et al. 1990) or other chromogens followed by UV irradiation (Spikes and Bommer 1993) or laser phototherapy (Castro et al. 1996). The aim of photodynamic therapy in these schemes is to use porphyrins for treatment, but not as a live vaccine as is intended in the present invention.

Mutant Porphyric Leishmania as Suicidal Vaccines

Figure 2:
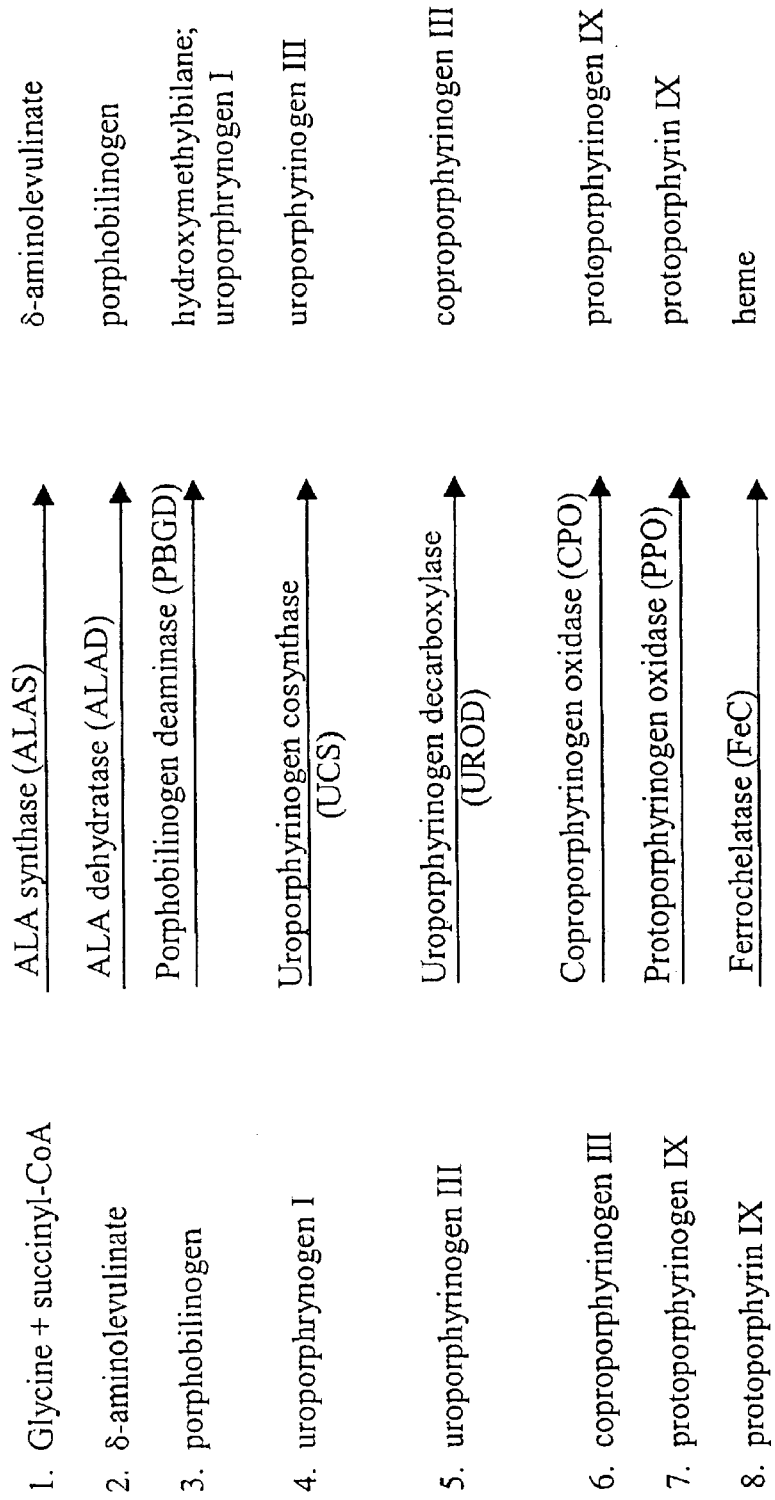
FIG. 2 is a summary of the enzymatic pathways for the biosynthesis of heme.

The use of porphyric Leishmania as a suicidal vaccine model emerged fortuitously as we examined trypanosomes for their unusual deficiency in heme biosynthesis. This was examined according to the following conventional heme synthesis pathway as shown in FIG. 2: glycine+succinyl-CoA or 4, 5 dioxovalerate+alanine→δ-aminolevulinate (ALA)→porphobilinogen (PBG)→hydroxymethylbilane [by-product=uroporphyrinogen I (URO)]→uroporphyrinogen III→coproporphyrinogen III→protoporphyrinogen IX→protoporphyrin IX→heme. FIG. 2 also lists the eight mammalian enzymes, which are known to catalyze this pathway (Sassa 2000). Their activities are often undetectable or negligible in trypanosomatid protozoa (see Sah et. al 2002). Reported elsewhere in these organisms were the negligible activities of ALA-synthase/dioxovalerate transaminase and intact ferrochelatase—the first and the last enzymes of the pathway normally present in mitochondria. Even less or completely absent are activities of the second and the third enzymes, i.e., δ-aminolevulinate dehydratase (ALAD) and porphobilinogen deaminase (PBGD). The pathway thus appears to be incomplete in this group of organisms. Endosymbionts are thought to complement this incomplete pathway in very few Crithidia spp. by supplying the missing enzymes.

It has long been known that this deficiency is manifested by their nutritional requirement in culture for heme compounds from exogenous sources. As aerobic cells, they require heme to serve as the prosthetic group of the respiratory protein complexes. Exceptional are a handful of insect trypanosomes, which naturally harbor endosymbionts to manufacture heme for them (Chang et al., 1975; Chang and Trager, 1974). In asymbiotic L. amazonensis, we have found that 7 of the 8 enzymes in the heme biosynthetic pathway are non-functional as shown in the schematic diagram of FIG. 10. This is expected in all trypanosomes, which normally are not infected with endosymbionts.

Because the overwhelming majority of wildtype trypanosomatids typically lack various enzymes associated with the heme synthesis pathway, these protozoa have the potential to be manipulated in such a way that porphyrin intermediates can accumulate at very high levels. A variety of schemes can be envisioned to accomplish this end, and thus the given scheme employed will depend on the preference of the practitioner of the present invention.

In a preferred embodiment, the mutant Leishmania species employed in the present invention is one that displays the following characteristics: (1) it has an ALAS-negative phenotype (See FIG. 2, Enzyme No. 1), (2) it has an ALAD-positive phenotype (See FIG. 2, Enzyme No. 2), (3) it has a PBGD-positive phenotype (See FIG. 2, Enzyme No. 3), and (4) it lacks at least one of the remaining five enzymes of the heme catalytic pathway (See FIG. 2, Enzyme Nos. 4-8). Pursuant to this embodiment, the above conditions are necessary for the accumulation of porphyrin intermediates.

The above scheme is premised on the fact that an exogenous ALA source will be used as a signal to induce a porphyric state. In this regard, due to the lack of the ALAS enzyme, the organism cannot independently produce ALA. The lack of ALA results in the absence of a substrate for the ALAD enzyme. The absence of endogenously-produced ALA therefore results in the subsequent absence of production of substrates that are involved in the enzymatic processes downstream from ALAS. Therefore, when ALA is neither endogenously produced nor available in the immediate environment, porphyrin intermediates cannot be produced and thus cannot accumulate in these protozoa.

As noted above, while the Leishmania must be deficient in the ALAS enzyme, the Leishmania must possess the ALAD enzyme and the PBGD enzyme. If these two enzymes are not present, the exogenously-administered ALA cannot be catalyzed to produce the subsequent products of porphyrin intermediates. When both enzymes are present, ALAD converts ALA to porphobilinogen, which is converted by PBGD into hydroxymethylbilanes that spontaneously form non-enzymatically uroporphrynogen I. In this regard, uroporphrynogen I is the first of the five porphyrinogen intermediates in the heme biosynthetic pathway.

As seen in FIG. 2, the other four subsequent porphyrin intermediates are uroporphyrinogen III, coproporphyrinogen III, protoporpliryrinogen IX and protoporphyrin IX. All porphyrinogens are present in cells under reduced conditions and are converted spontaneously into porphyrins in the presence of oxygen.

Assuming the presence of ALAD and PBGD, when ALA is exogenously supplied to the protozoa, at least one porphyrinogen intermediate will be produced, i.e., uroporphyrinogen I. However, if all additional enzymes (downstream of PBGD) of the heme synthetic pathway are present in a given organism, then the overall reaction pathway will progress efficiently and will ultimately result in the production of heme. In this case, the accumulation of porphyrin intermediates will not occur. It is therefore necessary that the organism lack at least one enzyme downstream of PBGD.

This most preferred embodiment of the present invention again employs mutants that (1) lack the ALAS enzyme, (2) possess the ALAD enzyme, (3) possess the PBGD enzyme, and (4) lack at least one heme synthetic pathway enzyme downstream of the PBGD enzyme. It must be stressed, however, that the present invention is not limited to the use of mutants that possess the above-four requirements. In this regard, the present invention is intended to encompass any scheme, in which a mutant trypanosomatid (genetically engineered or naturally occurring) is such that porphyrin intermediates can accumulate and subsequently cause autocytolysis of these protozoa due to the introduction of an external signal. Many such schemes can be envisioned. The guiding principles of such schemes, however, are that the phenotype of the mutant must be such that (1) the accumulation of porphyrinogen intermediates is induced by an external signal, and (2) once the production of porphyrinogen intermediates is initiated, accumulation of porphyrinogen intermediates occurs because at least one enzyme is lacking that would otherwise enable the porphyrinogen intermediates to ultimately be catalyzed for the formation of heme. This final product of the complete pathway is not photosensitive to UV irradiation for the generation of free radicals and is susceptible to disposal by heme degradation pathway.

Wildtype Leishmanias typically will not be suited for practicing the present invention. This is because wildtype Leishmanias typically do not posses the ALAD enzyme. Leishmania species useful for the present invention can be either naturally occurring mutants or genetically-engineered mutants.

Methods for screening naturally-occurring genetic and phenotypic mutants are well-known in the art.

Methods for engineering mutants suitable for practicing the present invention are also well-known in the art. In this regard, methods for such engineering include, but are not limited to "knock-out," "knock-in," and "blocking" methods at the gene level as well as anti-sense and RNAi inhibition of mRNAs at the translational level.

Porphyric mutants can be screened and/or constructed from non-pathogenic parasite species, e.g., guinea pig Leishmania enriettii, rodent Leishmania turinica, reptilian Leishmania torentolae; and avirulent strains of pathogenic Leishmania spp. The use of these organisms will alleviate the potential concern that the residual parasites, which survive the infection or UV irradiation, may cause leishmaniasis/parasitic diseases in the recipients. Avirulent L. major, for example, is a suitable choice, as it causes mild cutaneous infection, which becomes resolved spontaneously. Most of these organisms and their transfectants can be readily grown in simple available culture media and also in chemically defined media in liters for industrial scales.

Transfection of Leishmania with genes encoding additional porphyrin metabolizing enzymes will be useful to produce other types of prophyria with different species of porphyrins, e.g., coproporphyrins and protoprophyrin IX. Their different properties, e.g., hydrophobicity, will have relevance to cytoxicity and targeted delivery of such mutant constructs.

Lysis of Mutant Trypanosomatids

As noted above, an aim of the present invention is to eventual release of antigens from the Leishmania to immunize the host as a result of cytolysis of the porphyric mutant. Lysis can be induced by administration of exogenous ALA, for example. In this regard, ALA provides a substrate for the catalytic activity of the ALAD enzyme. Depending on the nature and extent of the downstream enzymes present in the heme biosynthetic pathway of the mutant, one or more porphyrin intermediates will accumulate, causing the mutant to eventually become porphyric. A natural consequence of sufficiently excessive porphyria will be lysis of the mutant. The administration of ALA to induce a state of porphyria therefore provides a time-controllable mechanism to provide release of the expressed peptide or protein of interest.

The external signal used to initiate porphyrin accumulation will depend on the overall scheme associated with the heme biosynthetic pathway enzymes present in the mutant. The external signal will therefore depend on the preferences of the practitioner of the present invention.

Administration of the external signal to initiate accumulation of porphyrin intermediates (e.g., administration of ALA) can be achieved by techniques that are well-known in the art. By way of example and not limitation, such administration techniques can include topical application, intramuscular injection, subcutaneous injection, intravenous administration and other parenteral, enteral, dermal routes of administration, inhalation, transbucal, and nasal administration.

Pursuant to the present invention, exposure of porphyric Leishmania to irradiation can result in a more rapid release of the peptide or protein sought to be delivered. In this regard, it is thought that exposure to irradiation of porphyric mutants hastens their rapid destruction via free-radical mediated cytolysis. To accomplish this end, the subject that carries the mutant must be exposed to irradiation. The optimal conditions associated with the irradiation exposure (e.g., wavelengths, duration, location, and intensity of the exposure) will vary depending on the preferences of the practitioner of the present invention and the target mammalian cells. A wide spectrum of light can be used for the irradiation, including but not limiting to, white, red, and ultra-violet (UV), which can be short-wave or long-wave UV.

Vaccination Against Leishmaniasis

A vertebrate subject can be vaccinated against leishmaniasis by administering to the subject with a vaccine comprising the mutant Leishmania as described above in the present invention. Once the subject receives the vaccine, the mutant Leishmania infects antigen-presenting cells (APC's), i.e., dendritic cells and macrophages, within the subject. The subject is then exposed to a first external signal to induce porphyria in the mutant Leishmania and causes cytolysis of the mutant Leishmania to release the antigens from the Leishmania in the APC to initiate the immunization process in the subject. Alternatively, the first external signal is used to induce porphyria while a second external signal is employed to cause cytolysis. In an embodiment, the mutant *Leishmania* is exposed to the first signal to induce porphyria but without cytolysis before administered to the subject.

In a preferred embodiment, the vertebrate subject is a mammalian subject, which can be, for example, a primate or a rodent. In another preferred embodiment, the mammalian subject is human.

In yet another preferred embodiment, the mutant *Leishmania* is selected or constructed to display the following characteristics: (1) it has an ALAS-negative phenotype (See FIG. 2, Enzyme No. 1), (2) it has an ALAD-positive phenotype (See FIG. 2, Enzyme No. 2), (3) it has a PBGD-positive phenotype (See FIG. 2, Enzyme No. 3), and (4) it lacks at least one of the remaining five enzymes of the heme catalytic pathway (See FIG. 2, Enzyme Nos. 4-8). Pursuant to this embodiment, the above conditions are necessary for the accumulation of porphyrin intermediates. Porphyria can be induced by administering ALA to the subject. The ALA is taken up by the mutant *Leishmania*, which is subsequently converted to one of the porphyrins described earlier, depending on the genetic make-up of the mutant *Leishmania*. The accumulation of porphyrin by the *Leishmania* will eventually causes cytolysis of the *Leishmania* when the ALA reaches a cytotoxic level for the *Leishmania*. In this embodiment, the ALA represents the first external signal. In another embodiment, cytolysis can be achieved more rapidly after the ALA administration by irradiating the mutant *Leishmania* with light of a selected wavelength. A wide spectrum of wavelength can be used for irradiation, including but limited to, white, red, and UV (both short-wave and long-wave UV). Irradiation can be accomplished by exposing the whole subject with the light. Alternatively, light can be directed to a specific internal organ of the subject via optic fiber. In this embodiment, the irradiation is the second external signal. In another embodiment, the mutant *Leishmania* is exposed to ALA to induce porphyria without cytolysis before the administration of the mutant *Leishmania* to the subject. Cytolysis is then initiated by irradiation of the mutant *Leishmania* after the *Leishmania* infects the APC's in the host subject.

EXAMPLE 1

Cell Cultures

Wildtype *Leishmania amazonensis* (LV78) promastigotes (clone 12-1) were grown at 25° C. in Medium 199 Hepes-buffered to pH 7.4 and supplemented with 10% heat-inactivated fetal bovine serum (HIFBS). Transfectants were grown under similar conditions with different concentrations of selective pressure, i.e., G418 and/or tunicamycin. Cells were also adapted to grow in a chemically defined medium. To initiate such cultures, cells were washed twice with the defined medium by centrifugation at 3,500 g for seeding at $2\text{-}5\times10^6$ cells/ml. Cells were counted using a hemacytometer. Macrophages (J774A1) were grown in RPMI 1640 supplemented with 10% or 20% heat-inactivated FBS at 35° C. Cultures of all cells rendered porphyric were kept in the dark to avoid cytolysis due to photosensitivity.

EXAMPLE 2

Cloning of the cDNAs

FIG. 3, which illustrates an example of an embodiment of the present invention, shows constructs of mammalian genes encoding porphobilinogen deaminase PBGD and δ-aminolevulinate dehydratase ALAD in p6.5 and pX vectors specific for transfection of *Leishmania*, respectively. Gray arrowed bars represent ampicillin resistance gene (AmpR). The thicker gray area is *Leishmania* DNA containing neomycin phosphotransferase gene (NeoR) and N-acetylglucosamine-1-phosphate transferase (NAGT) (dark arrowed bars) as selectable markers of *Leishmania* for G418 and tunicamycin, respectively. Arrow indicates the direction of transcription.

The cDNA of rat PBGD (1038 bp) (Accession # X06827) was obtained by digesting the plasmids with BamHI. The human ALAD (993 bp) (Accession # M13928) was amplified by polymerase chain reactions (PCR) from a cDNA cloned in pGEM-T vector using a high fidelity Taq polymerase (Expand Hi Fi, Boehringer). The forward and reverse primers used were SEQ ID NO:1 (5'-TGCCCACT GGATCCCCGCCATG-3') and SEQ ID NO:2 (5'-CACTG GGATCCATCATTCCTCC-3'). To facilitate cloning into the *Leishmania* expression vectors, the primer sequences were designed to include BamH1 sites (underlined) flanking the PCR products. The amplified products of alad was first cloned in pGEM-T for expansion and then gel-purified after BamHI digestion for cloning into *Leishmania*-specific vector, pX-neo. The rat pagd was cloned into p6.5 with N-acetylglucosamine-1-phosphate transferase gene or nagi for tunicamycin-resistance. The clones with the inserts in correct orientation were identified by restriction mapping. Promastigotes were transfected with pX-alad and/or p6.5-pbgd (see FIG. 3) by electroporation as described earlier, and selected initially for resistance up to 10 μg tunicamycin/ml or 20 μg G418/ml or a combination of both. Stable transfectants emerged in 8-10 days and were subsequently passaged continuously in media with appropriate drug pressures.

EXAMPLE 3

Western Blot Analysis

Stable transfectants grown in Medium199 supplemented with heat-inactivated FBS and selected with appropriate drugs were assessed for the presence of ALAD and PBGD by Western blot analysis. Briefly, protein samples each equivalent to $20\times10^6$ cells were subjected to SDS-PAGE using MiniProtean II (BioRad) and blotted to nitrocellulose. The primary anti-PBGD and anti-ALAD antisera were generated by immunization of rabbits with purified enzymes. Both were used at $1{:}10^5$ dilution. Peroxidase-conjugated goat anti-rabbit IgG (Sigma) was used as the secondary antibody. Immunoblots were subsequently developed with the ECL reagent (Amersham) and exposed to X-ray films.

Western blot analysis of various cell lysates revealed that both enzymes were undetectable in the wildtype (FIG. 4, Lane 1) and appeared as specific protein bands of the expected size (FIG. 4, Lanes 2-5) in the transfectants. Probing the blots with anti-ALAD antiserum alone revealed a single band of 36 kDa in the transfectants with pX-ALAD (Panel A, Lane 2) and those with this plasmid in combination with p6.5-PBGD (Panel A, Lane 5), but not in those with p6.5-PBGD and p6.5-PBGD+pX (Panel A, Lanes 3-4). Reprobing the same blot with anti-PBGD antisera showed that transfectants with pX-ALAD (Panel B, Lane 2), p6.5-PBGD (Lane 3) and p6.5-PBGD +pX (Lane 4) each contained single bands of the expected size, i.e., ~36 kDa or ~42 kDa, respectively, while those with both genes (Lane 5) contained both protein bands. The results thus indicate that both genes were expressed at the protein level individually in different transfectants and simultaneously in the same one using different vectors.

EXAMPLE 4

Enzyme and Porphyrin Assays

Cells were harvested by centrifugation for five minutes at 3,500 g, resuspended in phosphate buffer saline (pH 7.4) and lysed by three cycles of freezing-thawing in dry ice/acetone bath. Cell lysates equivalent to 20-50×10$^6$ cells and to 2-5×10$^6$ cells were used for ALAD assays and PBGD assays, respectively. The activity of ALAD was assayed by monitoring absorption at 553 nm for the color salt of porphobilinogen using the modified Ehrlich reagent. PBGD activities were assayed by a microfluorometric method. Porphyrin levels were determined fluorometrically using 5 μl of cell suspensions (=2-5×10$^6$ cells/ml) and 0.5 ml of 1 M perchloric acid/methanol (1:1, v/v). Samples were assayed for proteins using Coomassie R-250 dye-binding.

The type of porphyrins produced was determined by thin-layer chromatography (TLC) of relevant samples using porphyrin ester chromatographic marker kit as the standards (Porphyrin Products Co., Logan, Utah). Cells were grown in porphyrin-free chemically defined medium to 3-4×10$^8$ cells. Porphyrins were extracted from the cell pellets, methylated and analyzed by TLC.

Both ALAD and PBGD activities were absent in wildtype cells (not shown) and present only in transfectants with the genes of relevance (Table 1). The specific activities in pmol products/mg protein/hr fell within the range of ~2,500 to ~9,500 and ~400 to ~1,400 for ALAD and PBGD, respectively. The variations in the specific activities among different experiments seen may be accounted for by differences introduced inadvertently in the culture and selective conditions used. Clearly, both enzymes were fully functional alone or in combination in the transgenic *Leishmania* cells.

TABLE 1

ALAD and PBGD specific activities in *Leishmania* transfectants

| | ALAD activity (pmol PBG/mg protein/h) | | | PBGD activity (pmol URO/mg protein/h) | | |
|---|---|---|---|---|---|---|
| Expt. | $^1$transfectants containing: | | | | | |
| No. | alad | pbgd | alad & pbgd | alad | pbgd* | alad & pbgd |
| 1 | 9528 | 0 | 8187 | 0 | 1380 | 698 |
| 2 | 9230 | 0 | 6542 | 0 | 985 | 420 |
| 3 | 2660 | 0 | 3910 | 0 | 491 | 690 |

$^1$Grown to stationary phase in a defined medium and harvested for enzyme assays as described in Materials and Methods. See FIG. 1 for the plasmid constructs used for the transfection.
*Transfectants with the pX vector alone in addition to p6.5-pbgd.

Figure 5:
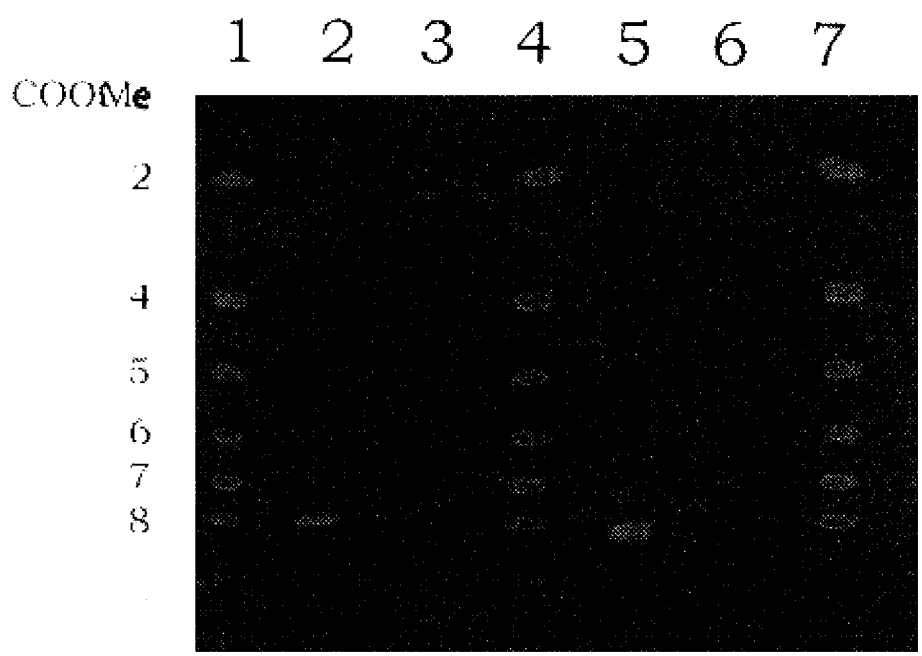
FIG. 5 shows a thin layer chromatogram showing uroporphyrin I in porphyric *Leishmania amazonesis* and that released from these cells.
Figure 6:
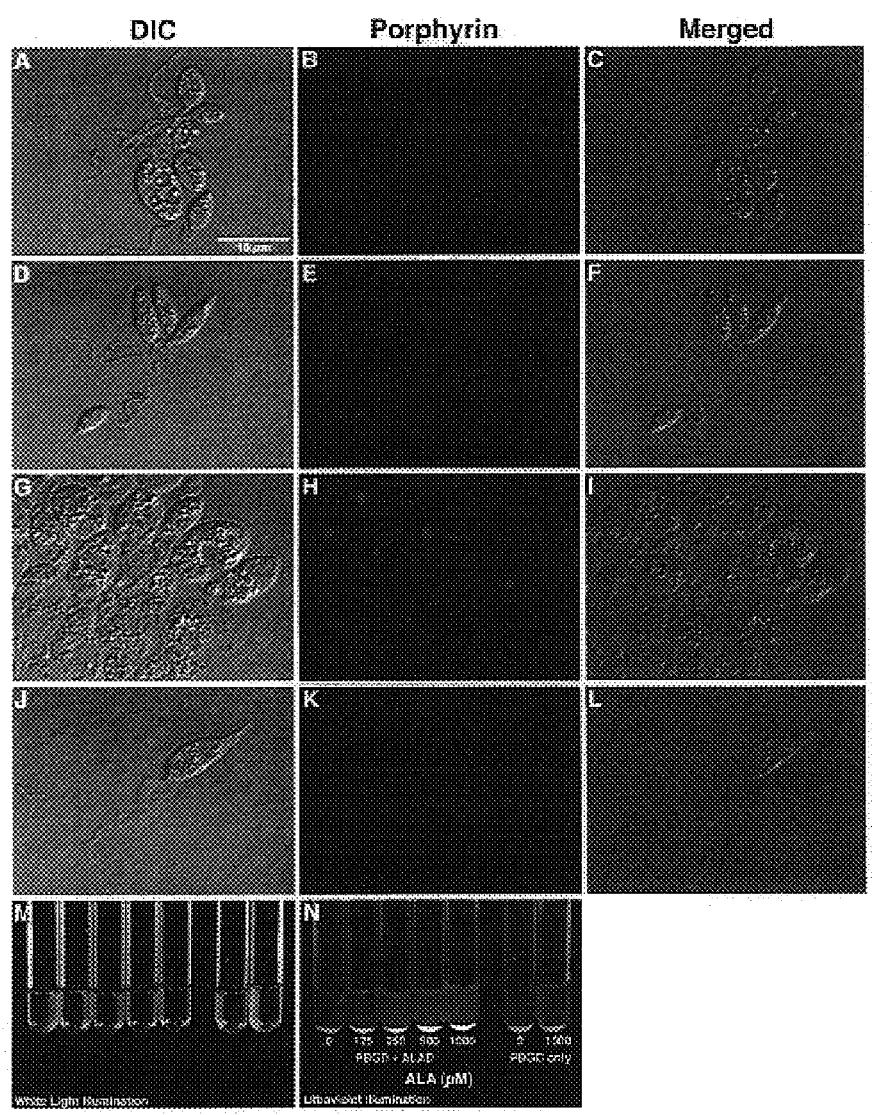
FIG. 6 shows the cellular localization of porphyrin in porphyric *Leishmania* amazonensis and ALA dose-dependent release of porphyrin from these cells.

While both ALAD and PBGD were expressed and fully active in *Leishmania* transfected with the respective gene, the transfectants produced no detectable porphyrins (see FIG. 5, Lanes 3 and 6; FIG. 6, Panel N, O ALA) unless ALA was provided to those with both transgenes (FIG. 5, Lanes 2 and 5; FIG. 6, Panel N 125-1000 μM ALA). However, this porphyric *Leishmania* along with all other transfectants resemble non-transfected wildtype cells in that they grew continuously only in the defined medium supplemented with either hemin or protoporphyrin IX (data not shown). Deletion of the heme compound from this medium resulted in the eventual cessation of their growth in all cases after several passages. Heme biosynthesis pathway thus remained incomplete in these transgenic *Leishmania*, clearly due to additional enzymatic defect(s) downstream of PBGD.

Uroporphyrin I was the sole intermediate detected in porphyric *Leishmania*. This was originally suggested by the fluorescence emission spectra of porphyrins extracted from porphyric *Leishmania* observed (data not shown) and confirmed by TLC analysis of these samples (FIG. 5). TLC of porphyrins extracted by standard procedures from porphyric *Leishmania* and their spent medium revealed only a single UV-fluorescent species (FIG. 5, Lanes 2 and 5), which co-migrated with uroporphyrin I octamethyl esters (Lanes 1, 4 and 7). This finding indicates that only uroporphyrin I was produced by these cells. No porphyrin bands were visible in samples prepared simultaneously from controls, e.g., transfectants with one or the other gene and their culture supernatants (FIG. 5, Lanes 3 and 6). The cells used for sample extraction were grown in porphyrin-free defined medium, eliminating the possibility that the porphyrin species detected may have derived from an exogenous source.

EXAMPLE 5

Porphyrin Fluorescence Microscopy

For all microscopic examinations of *Leishmania*, living cell suspension in 5-10 μl aliquots was placed on a glass slide and then covered with an 18 mm$^2$ glass coverslip. For routine examinations, the preparations were viewed under phase contrast for cellular structures in conjunction with epifluorescence for porphyrins using a filter set consisting of D405/10X (405 nm exciter), 485DCXR (485 nm dichroic) and RG610LP (610 nm emitter) (Chroma Tech Co, Brattleboro, Vt.) in a Zeiss standard microscope with super pressure mercury lamp (HBO 50 W, Osram). Images were obtained by confocal microscopy using an Olympus FluoView confocal microscope equipped with a Krypton/Argon mixed gas laser. Specimens were illuminated with the 488 nm excitation line. The specific fluorescent emission of the porphyrin was collected by a photomultiplier tube after passing through a 605 nm bandpass emission filter. Differential interference contrast (DIC) images were simultaneously collected using a transmission field detector coupled to a photomultiplier tube. Detection settings were determined using a negative control by adjusting the gain and offset settings to eliminate background. Images were collected using a 100× oil immersion objective (NA 1.40) with an electronic zoom of 3×. The confocal aperture was set to 5 mm to maximize the depth of field within the specimen. Digital image acquisition took approximately 7 seconds per frame, resulting in movement-induced blurring of the flagella in viable specimens. Images were composed in Adobe Photoshop. Only DIC images were adjusted for brightness.

The porphyrins emerged only in the double transfectants after the addition of ALA into their culture media. Porphyrin-specific signals were followed by epifluorescent microscopy and imaged by confocal fluorescent microcopy (see above for the settings used). By differential interference contrast microscopy, living cells under all conditions used appeared granulated with anterior flagella (FIG. 6, Panels A, D, G and J). Under the settings for confocal microscopy used for porphyrin, fluorescence signals emerged only in the double transfectants (FIG. 6, Panels H and K), but not in the control cells, e.g., the single transfectants with PBGD alone (Panels B and E). When the two sets of images from the same preparations were merged, porphyrin fluorescent signals appeared to be diffused in the cytosol (FIG. 6, Panel 1) as well as localized in cytoplasmic vacuoles (Panels I and L).

EXAMPLE 6

Accumulation and Release of Uroporphyrin

Figure 7:
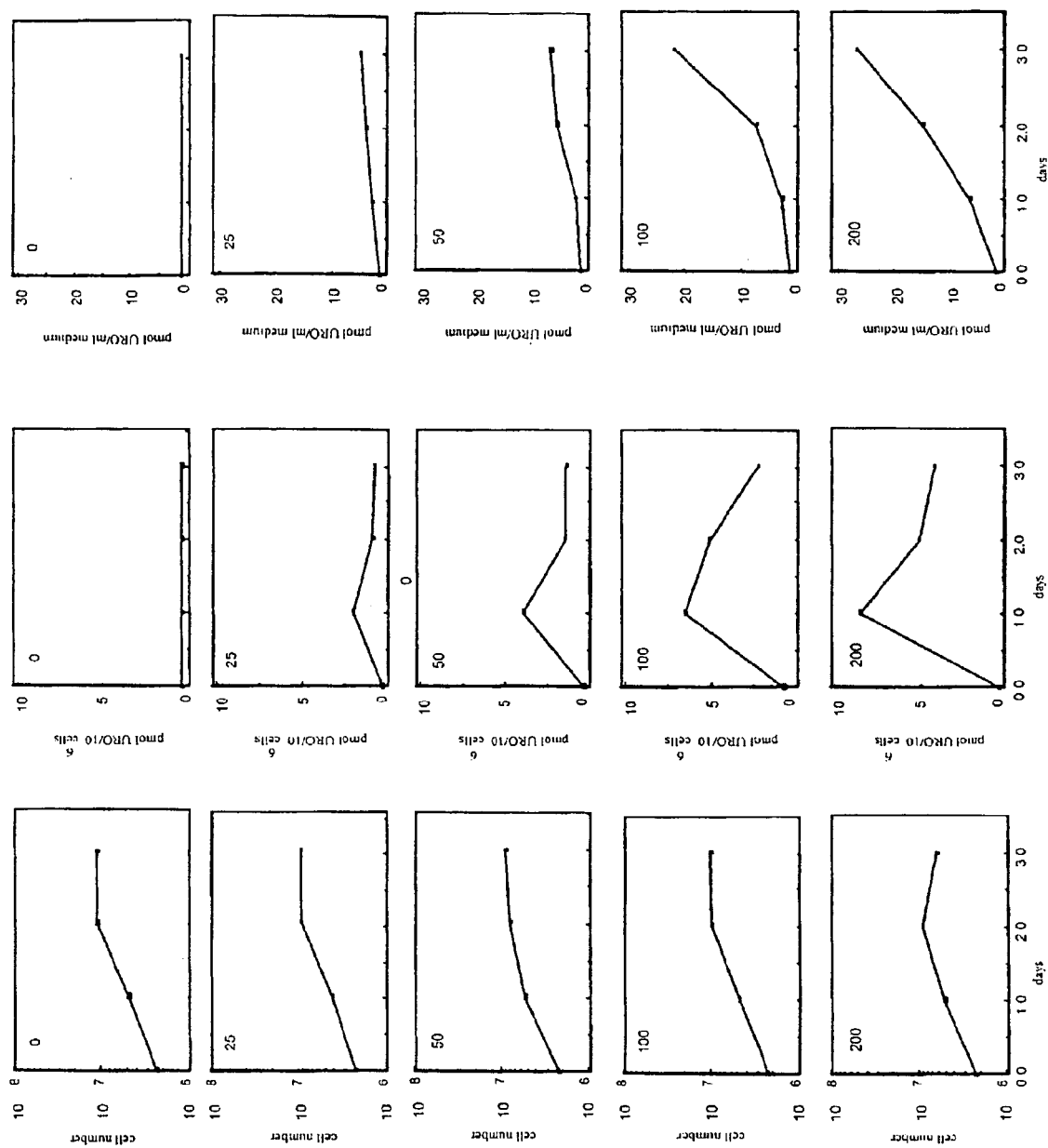
FIG. 7 shows the growth and porphyrin production of *Leishmania* doubly transfected with alad and pbgd in the presence of increasing ALA concentrations.

Porphyric *Leishmania* released uroporphyrin I into the medium, independent of cytolysis. This was demonstrated under two different conditions to generate modest and high levels of uroporphyria. Cells were handled gently to avoid inadvertent cytolysis. The kinetics of uroporphyrin accumulation in and release from porphyric *Leishmania* was quantitatively assessed fluorometrically. Initially used were cells grown in a chemically defined medium with a modest selective pressure of 2 µg tunicamycin and 10 µg G418/ml in conjunction with increasing, but low concentrations of ALA from 0 to 200 µM (FIG. 7). Under all these conditions, cells grew from $2.5 \times 10^6$/ml to $\sim 10^7$/ml in a period of three days (FIG. 7, Left panels), except the one with the highest ALA concentration of 200 µM, in which case the cell density decreases on day 3 (FIG. 7, Bottom left panel). In the absence of ALA, porphyrin was detected neither in cells nor in their spent media throughout the period of cell growth (FIG. 7, Top middle and right panels). In the presence of ALA, the cells produced uroporphyrin in an ALA dose-dependent manner, namely an increase from ~3 to ~8 pmol uroporphyrin/$10^6$ cells in the presence of 25 to 200 µM ALA during the first day (FIG. 7, Middle Panels). The cellular levels of uroporphyrin declined in these cells from day 2 to day 3, concomitant with its release also in an ALA dose-dependent manner from 5 to 28 pmol uroporphyrin/ml in the culture medium (FIG. 7, Right Panels).

In a separate set of experiments, cells were grown in Medium 199 plus heat-inactivated FBS under the optimal conditions for uroporphyria, i.e., a 10-fold increase of the selective pressure (20 µg tunicamycin and 100 µg G418/ml) and a 5- to 8-fold increase of the substrate (up to 1.0-1.6 mM ALA provided exogenously). Under these conditions, both cellular and released uroporphyrin levels were considerably enhanced (FIG. 6, Panels N 125-1000 µM ALA), the latter reaching a level as much as ~2 µM. Cytolysis was observed in <1% of these cells that did not account for the level of porphyrin release seen.

The results from both sets of the experiments indicate that uroporphyria was induced in an ALA dose-dependent fashion, which was marked by initial cellular accumulation of uroporphyrin followed by its release and accumulation in the culture medium.

EXAMPLE 7

UV Sensitivity Assays

For these experiments, transfectants with ALAD and PBGD, and those with the latter alone were grown in chemically defined medium supplemented with up to 1.6 mM ALA to generate different levels of porphyria. Cell suspensions in 24 well microtiter plates ($10^7$ promastigotes/ml/well or $5 \times 10^6$ promastigotes+$5 \times 10^5$ J774A1 macrophages/ml/well) were irradiated after infection or immediately at room temperature under a longwave UV lamp (254-366 nm multi-bands, Mineralight Lamp, Model UVSL-58, Ultraviolet Products, Inc, San Gabriel, Calif.) placed ~5 cm above the cell layers. Porphyric *Leishmania* prepared under other conditions and their spent media with different concentrations of released porphyrins were also examined for their effects on J774A1 cells. After illumination for variable time periods, cells were microscopically examined immediately. Cells of the monocytic tumor line were counted using a hemacytometer 1-2 days after irradiation. All experiments were repeated at least twice.

Porphyric *Leishmania* remained motile and thus viable under all culture and selective conditions used, except when they were subjected to UV irradiation. This sensitivity was indicated by the immediate cessation of the motility of the early porphyric cells after exposure to illumination under the setting for epifluorescent microscopy or with the long wave UV lamp. Late porphyric cells exposed to ALA two days or longer were less sensitive, while non-porphyric cells were totally insensitive to UV irradiation under these conditions, as indicated by their motility.

Figure 8:
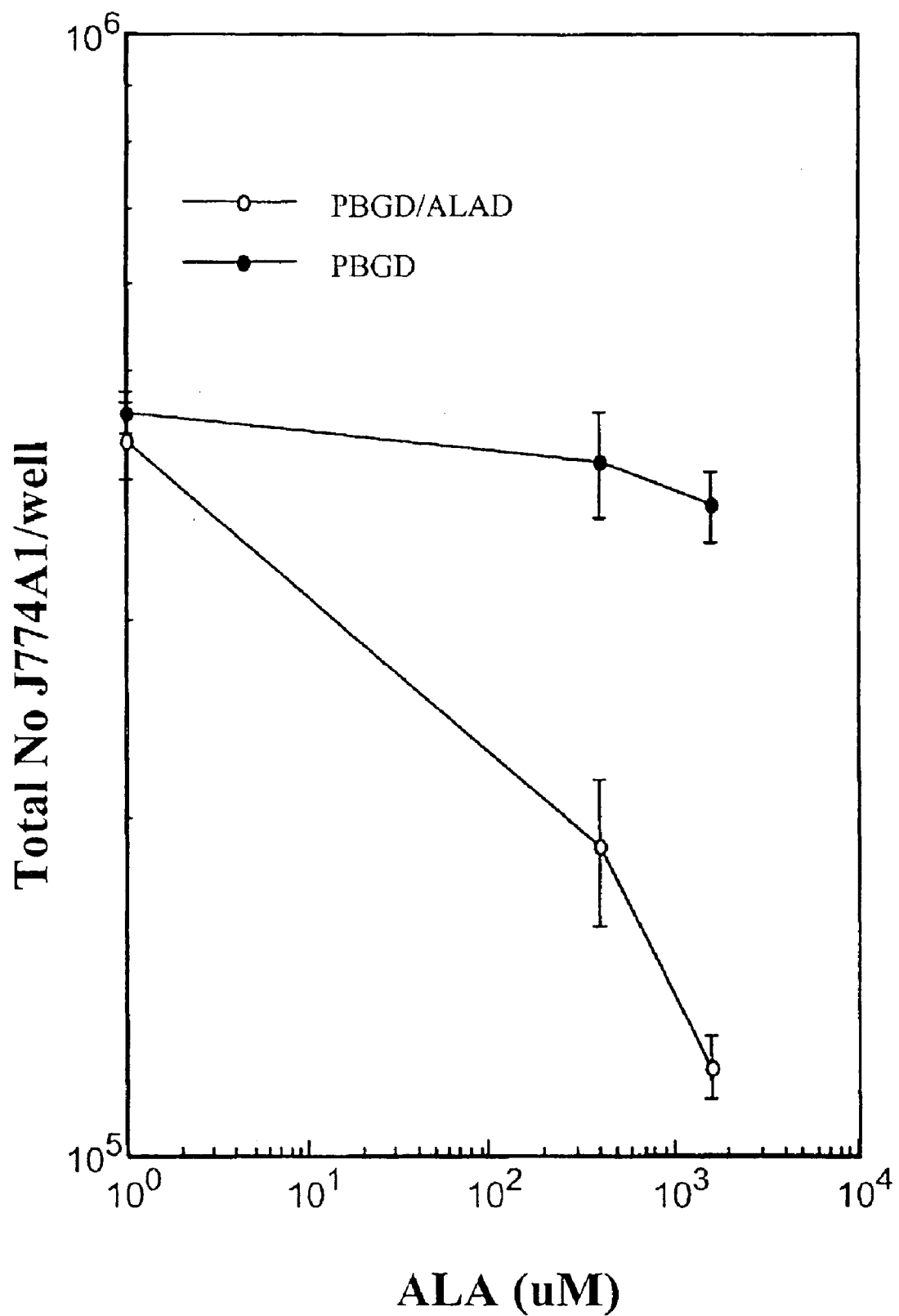
FIG. 8 shows cytolysis of J774A1 monocytic tumor cells exposed to porphyric *Leishmania*.

The monocytic tumor cells, J774A1 cells were also rendered sensitive to long wave UV irradiation after infection with porphyric *Leishmania*. Used for these experiments were double transfectants with both ALAD and PBGD, and single transfectants with only the latter gene grown under the same conditions, uroporphyria being generated only in the former. The results (FIG. 7) showed that UV irradiation lysed only the macrophages infected with porphyric *Leishmania*; and that the cytolysis was proportional to the porphyric levels of the latter modulated by prior exposure to different ALA concentrations (FIG. 8, ALAD/PBGD). The non-porphyric *Leishmania* produced no such effect (FIG. 8, PBGD), regardless of their exposure to ALA and UV irradiation under the same conditions. There was also no cytolysis of the tumor cells when irradiated immediately after mixing them with the porphyric *Leishmania* or in the presence of their spent media containing uroprophyrin I. The results obtained from these experiments were similar to the control in FIG. 8 (not shown).

EXAMPLE 8

Expression of a Transgene Product

The experiments began with infecting macrophages of the J774 line with *Leishmania* doubly transfected with pX-alad and P6.5-pbdg. The selectable marker of the vector pX contains neo for expression of neomycin phosphotransferase (NEO), conferring G418-resistance on the transfectants. After infection for ~7 days, the culture was split into two sets, which were treated with and without 1 mM ALA overnight, respectively. As expected, UV fluorescent microscopy revealed that porphyrins were absent in the set without ALA treatment and present at high intensity in both macrophages and *Leishmania* of the other set treated with ALA. Both sets were subsequently incubated in the absence of ALA for 3 days so that porphyrins diminished in the macrophages to the background level, but remained highly elevated in the *Leishmania*. All cultures were then exposed to UV irradiation under conditions as described (Sah et al. 2002). Notably, UV irradiation under these experimental conditions used selectively lysed only the porphyric *Leishmania* inside the macrophages, but not the latter. This was in contrast to cytolysis of macrophages observed when they were infected with the double transfectants already rendered porphyric before infection (FIG. 8). The different experimental conditions used may produce very different photodynamic properties of uroporphyrin I, accounting for the differential outcomes observed. Cells processed under the current conditions were then fixed with 4% paraformaldehyde for evaluating NEO release from intracellular *Leishmania* by immunocytochemistry. This was carried out by the standard protocol using rabbit anti-NEO antiserum as the first antibody and biotinylated donkey anti-rabbit as the second antibody, both at 1:500 dilution. The reaction products were developed with streptavidin-Cy3. Cells were counter-stained with Sytox Green for nuclear fluorescence. Cell preparations were examined by confocal microscopy as described (Sah et al. 2002), except for the excitation wavelengths used, which were 488 nm and 568 nm for Cy3 and Sytox Green, respectively. Images were collected from 8 profiles of 0.25 μm and merged.

Figure 9:
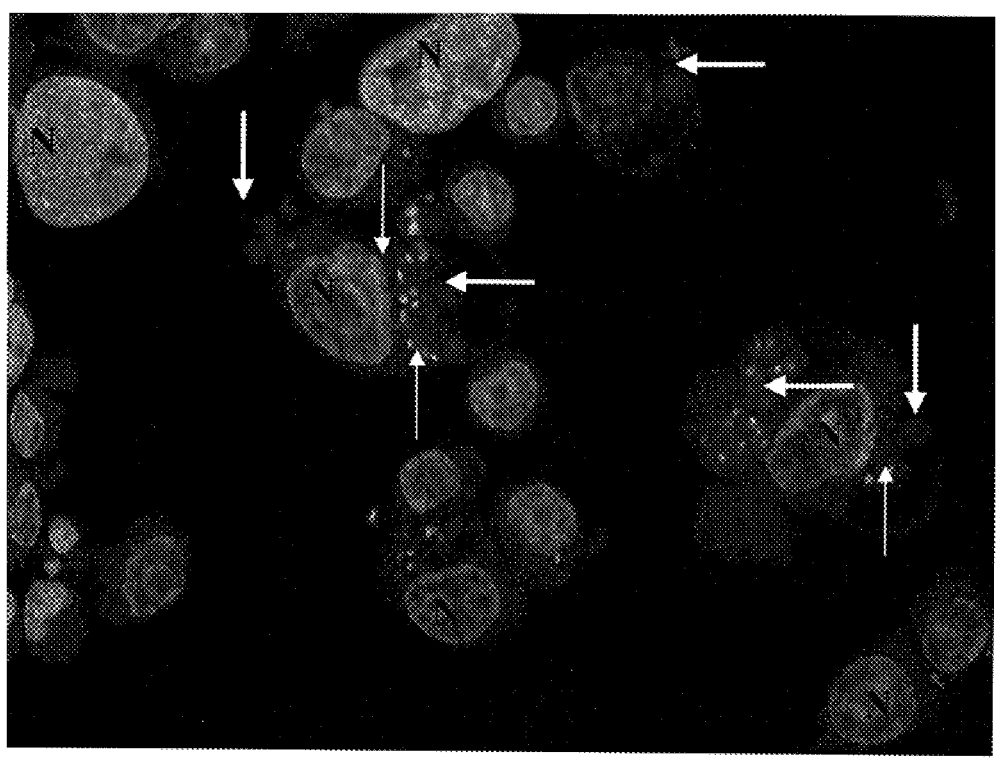
FIG. 9 shows selective lysis of intra-macrophage *Leishmania* rendered porphyric with ALA followed by UV irradiation to release expressed episomal gene products of neomycin phosphotransferase.

FIG. 9 shows the release of a neomycin phosphotransferase gene product (NEO) from porphyric Leishmania into the cytosol of infected host cells. Macrophages of J774 line were infected with Leishmania doubly transfected with P6.5-pbgd and pX-alad where pX vector contained a selectable marker—neo. The products of this gene, NEO, were examined for their release from porphyric Leishmania in the infected macrophages as an example. The infection was allowed to establish for 7 days before induction of porphyria by ALA treatment and UV irradiation, as described. Before UV irradiation, all cultures were kept for 3 more days in ALA-free conditions whereby porphyrins return to the background level in macrophages, but remained elevated in intracellular Leishmania. Controls were simultaneously prepared by omitting ALA treatment. All samples were fixed briefly with 4% paraformaldehyde and processed for immunocytochemistry by standard procedures using rabbit anti-NEO as the first antibody and biotinylated donkey anti-rabbit IgG as the second. Samples were developed by using streptavidin-Cy3 for reaction products of NEO and counterstained with Sytox Green for nuclei. Images were collected by confocal microscopy using appropriate wavelengths for the respective dyes used.

The Cy3 signals in orange red for NEO were seen at high intensity in infected macrophages only when treated with ALA followed by UV irradiation (see FIG. 9). These signals were absent or negligible in controls, i.e., the same materials without ALA treatment (Not shown). NEO signals appeared in the cytoplasm of some infected cells, but were not co-localized with the green fluorescence for Sytox in their nuclei (FIG. 9, N). This was consistent with the known residence of Leishmania in the cytoplasmic vacuoles of infected cells. There were patches of orange red fluorescent clusters in the cytoplasmic clear area, corresponding to aggregates of Leishmania in parasite-containing vacuoles. Each red-orange fluorescent cluster was interspersed with green-fluorescent dots, indicative of Leishmania DNA containing structures, i.e., parasite nuclei and kinetoplasts (=mitochondrial DNA) (FIG. 9, thin arrows). These Leishmania nuclei/kinetoplasts were absent in some individual structures in the orange-red cluster (FIG. 9, thick arrows), which clearly represented lysed Leishmania whence NEO release was expected. The released NEO was apparently insufficiently soluble or insufficiently fluorescent in the parasite-containing vacuole, which would otherwise fluoresce orange red. Although NEO in apparently lysed Leishmania stayed aggregated, some orange red fluorescence appeared in other part of the cytoplasm. This suggested diffusion of NEO into other cytoplasmic vacuoles and/or into the cytosolic compartment. If so, the released products from Leishmania would be accessible to both MHC-class I and MHC-class II pathways of antigen presentation. This is important in considering the potential use of porphyric Leishmania for delivering vaccines.

EXAMPLE 9

Transgenic Leishmania as a Suicidal Vaccine

Figure 10:
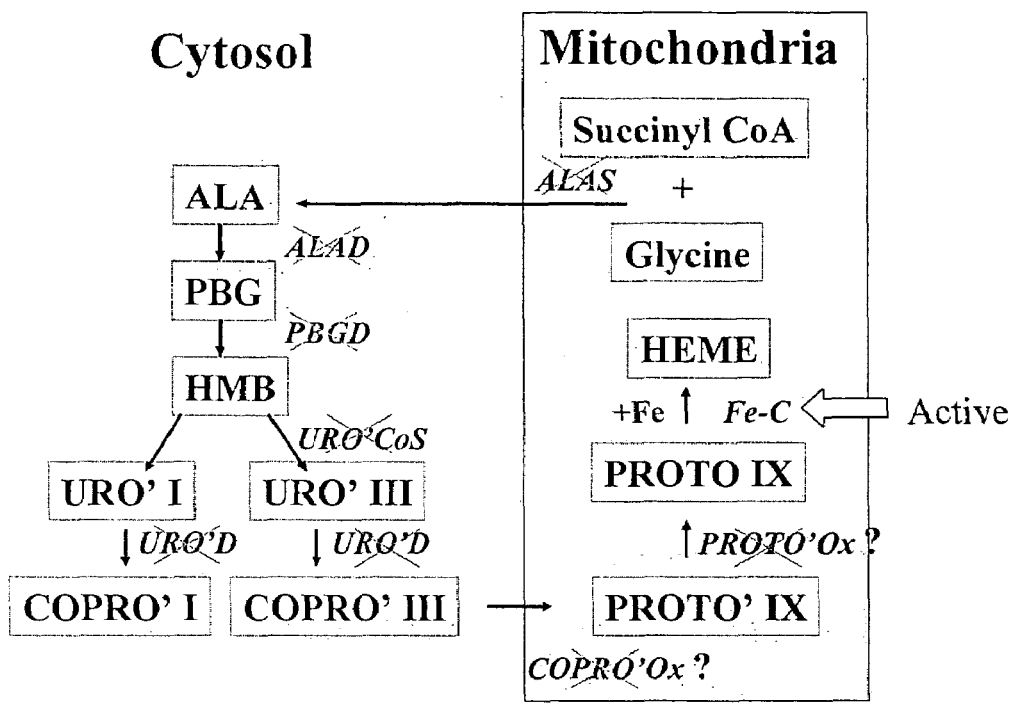
FIG. 10 is a schematic diagram showing the incomplete biosynthetic pathway of trypanosome.
Figure 12:
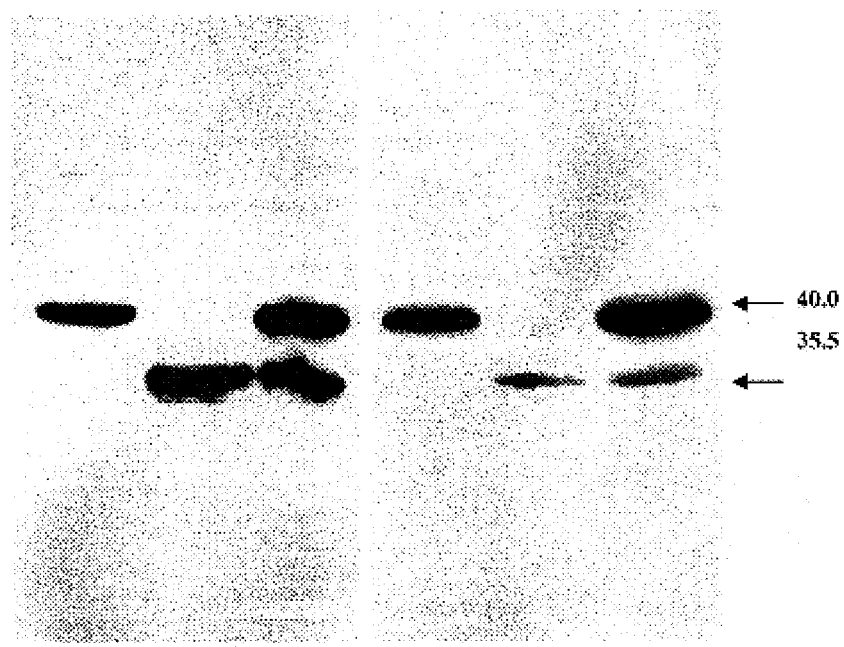
FIG. 12 is a Western blot analysis showing *Leishmania* transgenic expression of human aminolevulinate dehydratase (alad) and rat porphobilinogen deaminase (pbgd). cDNAs were cloned into *Leishmania*-specific vectors, pX and p6.5, respectively. Transfection of *Leishmania* promastigotes with these constructs singly or in combination by electroporation was followed by selection with drugs specific to the markers used, resulting in stable transfectants, which produce PBGD of ~40 kDa (Lanes 1, 4) or ALAD of ~36 kDa (Lanes 2, 5) or both (Lanes 3, 6). Proteins equivalent to $10^7$ promastigotes loaded per lane.
Figure 13:
FIG. 13 shows ALA-induced uroporphyria of *L. amazonensis* promastigotes doubly transfected with alad and pbgd. 108 living cells/ml in HBSS-HEPES (pH 7.4)+0.01% BSA and 1 mM ALA for 2 days in darkness. Upper panel, phase contrast (~800×); Lower panel, porphyrin fluorescent microscopy. Chroma filter set: 405 nm Excitation (D405/10×), 485 nm Dichroic (485 DCXR), 610 nm Emission (RG610LP)
Figure 14:
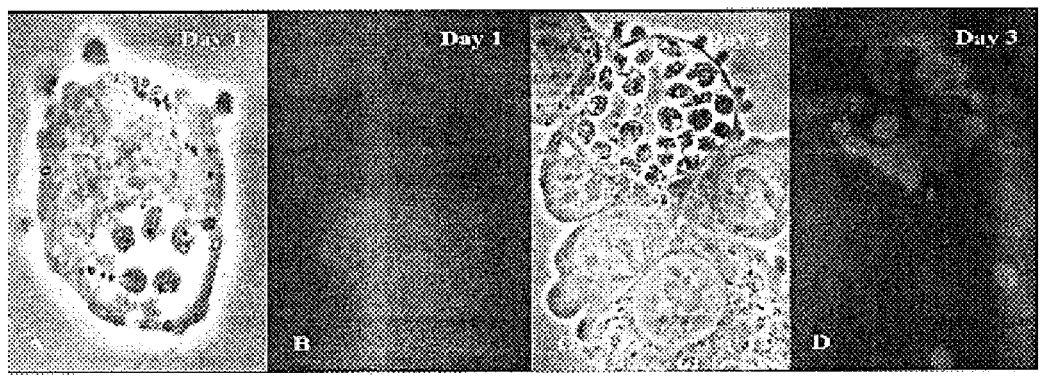
FIG. 14 shows ALA-induced uroporphyria of intra-macrophage transgenic *Leishmania*. alad/pbgd double transfectants of *L. amazonensis* infect J774A1 macrophages and produce large parasitophorous vacuoles (A, C) wherein promastigotes differentiate into amastigotes. Addition of 1 mM ALA to these infected cells results in initially modest porphyria of macrophages (B, Day 1) followed by intensive and persistent uroporphyria of intravacuolar amastigotes. A, B: Phase contrast; C, D: Porphyrin fluorescence (see legend to FIG. 13 for filter setting)
Figure 15:
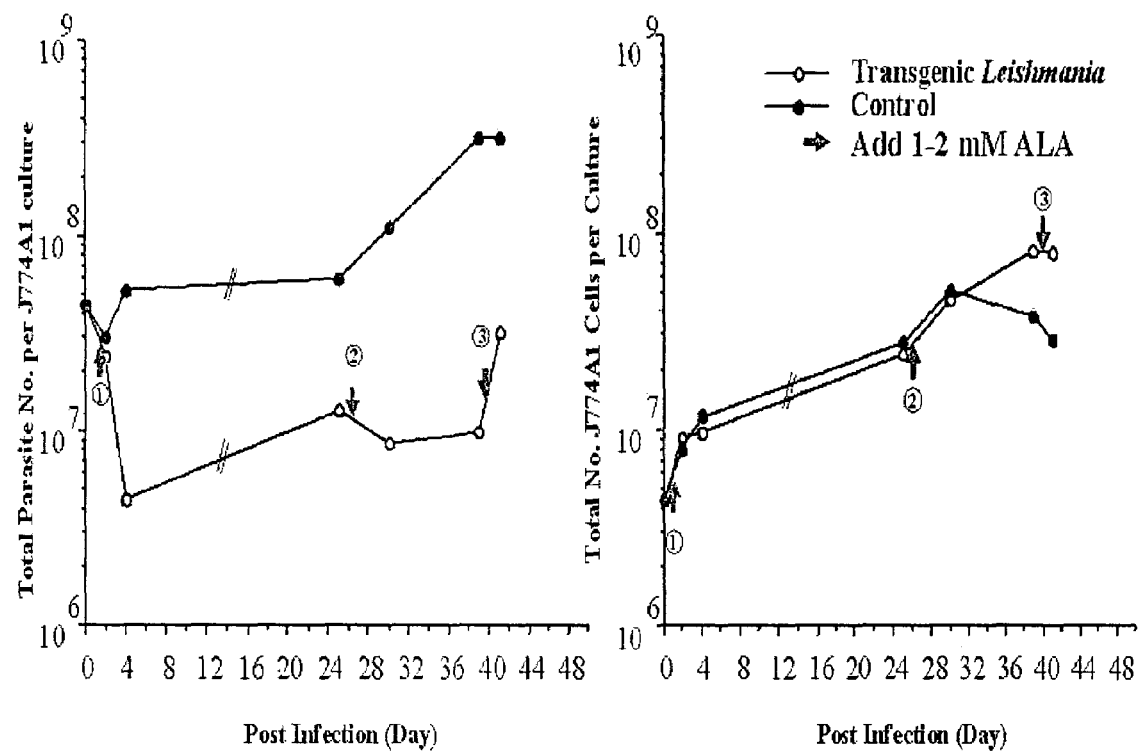
FIG. 15 shows the lysis of intracellular transgenic *Leishmania* in response to ALA added to infected macrophages. J774A1 cells were infected in vitro with alad/pbgd double transfectants of *L. amazonensis* at a promastigote-to-macrophage ratio of 10:1. Infected cultures were maintained at 35° C. with daily medium renewal for 42 days. Cultures were split equally into two, one with and the other without the addition of 1-2 mM ALA 3 times on days 2, 26 and 40 post-infection (arrows). The total number of intracellular amastigotes (left) and macrophages (right) per culture were estimated at the time points indicated, as described (Chang, 1980). Note: Decrease of intracellular amastigotes in number after the $1^{st}$ 2 ALA treatments. No such effect was seen when single transfectants were used.

Promastigotes of L. amazonensis were episomally transfected with mammalian genes (alad and pbgd) (FIG. 11), encoding the $2^{nd}$ and the $3^{rd}$ enzymes in the heme synthetic pathway (FIG. 2). Enzymatically active proteins (Table 1) of the expected size (FIG. 12) are produced in these double transfectants. They become highly porphyric (HMB=hydroxymethyl bilane spontaneously converted into uroporphyringen I autooxidized to uroporphyrin I) (Table 2; FIG. 13) when exposed to exogenously supplied delta-aminolevulinate (ALA)—the products of the $1^{st}$ enzyme, ALAS, in this pathway (FIGS. 2 and 10).

TABLE 2

Stable transfectants of Leishmania spp. are inducible with ALA for developing uroporphyria

| Leishmania spp | Transfection with: alad | Transfection with: pbgd | Porphyrin (pmol/$10^6$ cells) |
|---|---|---|---|
| amazonensis | + | − | 0.000 |
|  | − | + | 0.000 |
|  | + | + | 3.33 ± 1.0 |
| major | + | − | 0.000 |
|  | − | + | 0.000 |
|  | + | + | 8.80 |
| infantum | + | − | 0.000 |
|  | − | + | 0.000 |
|  | + | + | 3.10 |
| donovani | + | − | ND* |
| enriettii | + | − | ND* |

(*ND: not done)

Uroporphyric Leishmania promastigotes are extremely light-sensitive, as determined by fluorescent microscopy assay for inhibition of their motility. Aliquots of ALA-treated $10^8$ cells/ml in HBSS+HEPES (pH 7.4) and 0.01% BSA as described were placed under coverslips on glass slides and exposed under 100× oil immersion lens to illumination at the setting for porphyrin (405 nm excitation; 610 nm emission) by epifluorescence microscopy. Flagellum motility of >100 cells was assessed per sample before and after light exposure. Data in triplicate from two independent experiments are shown in Table 3, indicating that the light-sensitivity of Leishmania promastigotes doubly transfected with alad/pbgd is due to de novo cytosolic emergence of uroporphyrin I in response to ALA, as determined by microscopic assay for loss of flagellum motility. For this assay, double transfectants were first exposed to ALA for 2 days to render them uroporphyric and then illuminated microscopically under conditions described above. These uroporphyric cells are uniformly fluorescent (FIG. 13). After illumination for as short as 15 sec, flagellum ceased to beat in ~85% of these cells (Row 1), but remained active in all control groups, i.e., double transfectants without ALA treatment or without illumination and transfectants with plasmid alone exposed to both (Rows 2-4). The irradiated uroporphyric promastigotes eventually underwent cytolysis and failed to grow upon cultivation. Excitation of porphyrins with light is well-known to generate singlet oxygen and other free radicals (34, 74) accounting for the cytotoxicity observed.

TABLE 3

Light-sensitivity of *Leishmania* promastigotes doubly transfected with alad/pbgd is due to de novo cytosolic emergence of uroporphyrin I in response to ALA, as determined by microscopic assay for loss of flagellum motility

| Transfection | 1 mM ALA (2 days) | Irradiation (15 sec) | % Immobilization |
|---|---|---|---|
| alad/pbgd | + | + | 85.05 ± 4.52 |
| alad/pbgd | + | − | 00.60 ± 0.70 |
| alad/pbgd | − | + | 00.00 ± 0.00 |
| vector alone | + | + | 00.00 ± 0.00 |

These transgenic *Leishmania* are thus mutants inducible to commit suicidal cytolysis by exposure to external signals of ALA and light. Application of these inducers at varying strengths or intensities further provides the potential modalities to regulate cytolysis of these suicidal mutants. It is possible to create a spectrum of aporphyric to hyperporphyric cells by simply exposing them to different ALA concentrations, since there is no feed-back inhibition or allosteric hindrance of the transgenic enzymes (FIGS. 2 and 10). Illumination of porphyric cells at different light intensities, wavelengths and periodicity can further modulate the timing and degrees of their cytolysis.

Additional transfectants have been prepared from four other *Leishmania* spp. selected for their known differences in infectivity (Table 2). Similar to those prepared previously from *L. amazonensis* (Sah et al., 2002), they all become uroporphyric in response to ALA, but only when transfected doubly with both alad and pbgd, i.e., *L. infantum* and *L. major*. Single transfectants of these and other species (*L. donovani* and *L. enriettii*) with either of the 2 genes are all ALA-unresponsive. It appears from these data that all *Leishmania* spp. are equally defective in heme biosynthesis (FIG. 10). In addition, we have also started to obtain triple transfectants using a $3^{rd}$ vector to express UROD, the $5^{th}$ enzyme in the heme biosynthesis pathway. Such triple transfectants are expected to produce coproporphyrin I, which is more hydrophobic than uroporphyrin I.

The transgenic *Leishmania* remains responsive to ALA to become uroporphyric after infection of macrophages in vitro and in vivo (FIG. 14). These observations provide key evidence to support our consideration of using these mutants as a live vaccine model. The double transfectants of *L. amazonensis* (Sah et al., 2002) were used to infect macrophages from the following sources: [1] mouse tail base dermis (infected subcutaneously beforehand in vivo for 3 days); [2] mouse peritoneal cavity; [3] human peripheral blood monocytes; and [4] cultures of J774A1 macrophage cell line (originally from the peritoneal cavity of BALB/c mouse). Bulk of the work was carried out with the cell line, because of the ease to obtain these cells in culture and because of our experience with them for *Leishmania* infection. The double transfectants infect these macrophages and produce large parasitophorous vacuoles in 2-3 days (FIGS. 14A and C, phase contrast). When such infected cultures were exposed to 1 mM ALA overnight, both macrophages and their intravacuolar amastigotes developed a modest level of porphyria (FIG. 14B day 1). ALA treatment was removed by daily medium renewals for maintaining these infected cultures. Thereafter, porphyrin fluorescence diminishes rapidly in macrophages, but increased and persisted at high intensity in intracellular amastigotes (FIG. 14D). This outcome of host-parasite disparity in porphyric levels is fully expected. Macrophages metabolize porphyrins rapidly, since their heme biosynthesis and degradation pathway is intact. With only ALAD and PBGD from their episomal transgenes (FIG. 11), the intracellular amastigotes utilize exogenously supplied ALA to form uroporphyrin I, which accumulates as the end products due to the absence of the downstream enzymes of the pathway (Sah et al., 2002). Notable from these studies is also the accessibility of the intracellular amastigotes to the exogenously supplied ALA, which is apparently transported effectively not only by the plasma membrane of the infected macrophages but also across their parasitophorous vacuolar membranes and the amastigote plasma membranes. This ALA-induced porphyria of intra-macrophage amastigotes occurs only when macrophages are infected with double transfectants, but not with wildtype *Leishmania* or single transfectants with either alad or pbgd alone. Porphyrins produced by macrophages appear in their cytoplasm, but are not transferred to the amastigotes in parasitophorous vacuoles.

Intra-macrophage amastigotes are lysed selectively when rendered uroporphyric in situ, as determined by quantitative analysis of parasites and macrophages in such infected cultures (FIG. 15). This observation further strengthens the use of porphyric *Leishmania* as a live model for vaccine delivery. We observed this by using macrophages infected with the double transfectants. The infected cultures were split equally into 2 identical sets. In a total period of 42 days, one set received 3 separate ALA treatments, each pulsed for ~24 hrs, at different time points after infection, while the other set received no treatments (see legend to FIG. 15 for experimental conditions). The total number of intracellular amastigotes and macrophages per culture were enumerated microscopically shortly before and after ALA treatments. The results clearly showed that the intracellular amastigotes decrease in number in the ALA-treated culture and increase in ALA-untreated one after the $1^{st}$ 2 treatments (FIG. 15 Left panel $1^{st}$ 2 arrows). Uroporphyria of the intracellular amastigotes develops only in ALA-treated set (FIG. 14D), thereby accounting for their decrease in number therein. The development of uroporphyria alone appears to cause degeneration/cytolysis of these intracellular amastigotes, since these cultures were not specifically exposed to light for sensitizing porphyrins to generate cytolytic free radicals. However, the contribution of phototoxicity cannot be totally ruled out, since these cultures were not handled and observed in total darkness. Exposure of these cultures to longwave UV irradiation, indeed, hastens the cytolysis of uroporphyric amastigotes in infected cells. The intracellular amastigotes in these cultures remain ALA-inducible to develop uroporphyria for cytolysis for as long as 26 days after infection (FIG. 15 Left panel $2^{nd}$ arrow), but not after 42 days ($3^{rd}$ arrow). The transgenes and/or their products in these intracellular amastigotes thus appear to have lost their threshold level of functionality sometime between 26 and 42 days post-infection. This loss is expected to occur from a decrease of the plasmids in copy number as the transfectants grow in the absence of selective pressure intracellularly in macrophages. The longevity of the intracellular transfectants in ALA-responsiveness for 26 days provides a wide window of opportunity to induce their porphyria-mediated suicidal cytolysis at different levels. Clearly, uroporphyria develops far more intensely in response to ALA on day 2 than on day 26 after infection of macrophages, leading to sharp and shallow decreases of their intracellular amastigotes, respectively (FIG. 15 Left panel $1^{st}$ 2 arrows). Significantly, the growth of J774A1 macrophages is unaffected by ALA. They grow equally well with or without ALA (FIG. 15 Right panel) (except after prolonged incubation when *Leishmania* infection becomes too heavy toward the end). This is in sharp contrast to the dramatically different fate of their intracellular *Leishmania* transfectants under the same experimental conditions. Exposure of non-infected macrophages alone to ALA induces only modest porphyria, which dissipates rapidly for the presence of intact heme metabolic pathway in these cells. This rapid metabolism of porphyrins by the host cells coupled with a persistence of uroporphyria in the intracellular *Leishmania* transfectants creates their differential sensitivity to ALA-induced cytolysis selectively against the latter. This selectivity can be further regulated by exposure to light, resulting in the lysis of intracellular amastigotes with their host macrophages left virtually unscathed.

Figure 16:
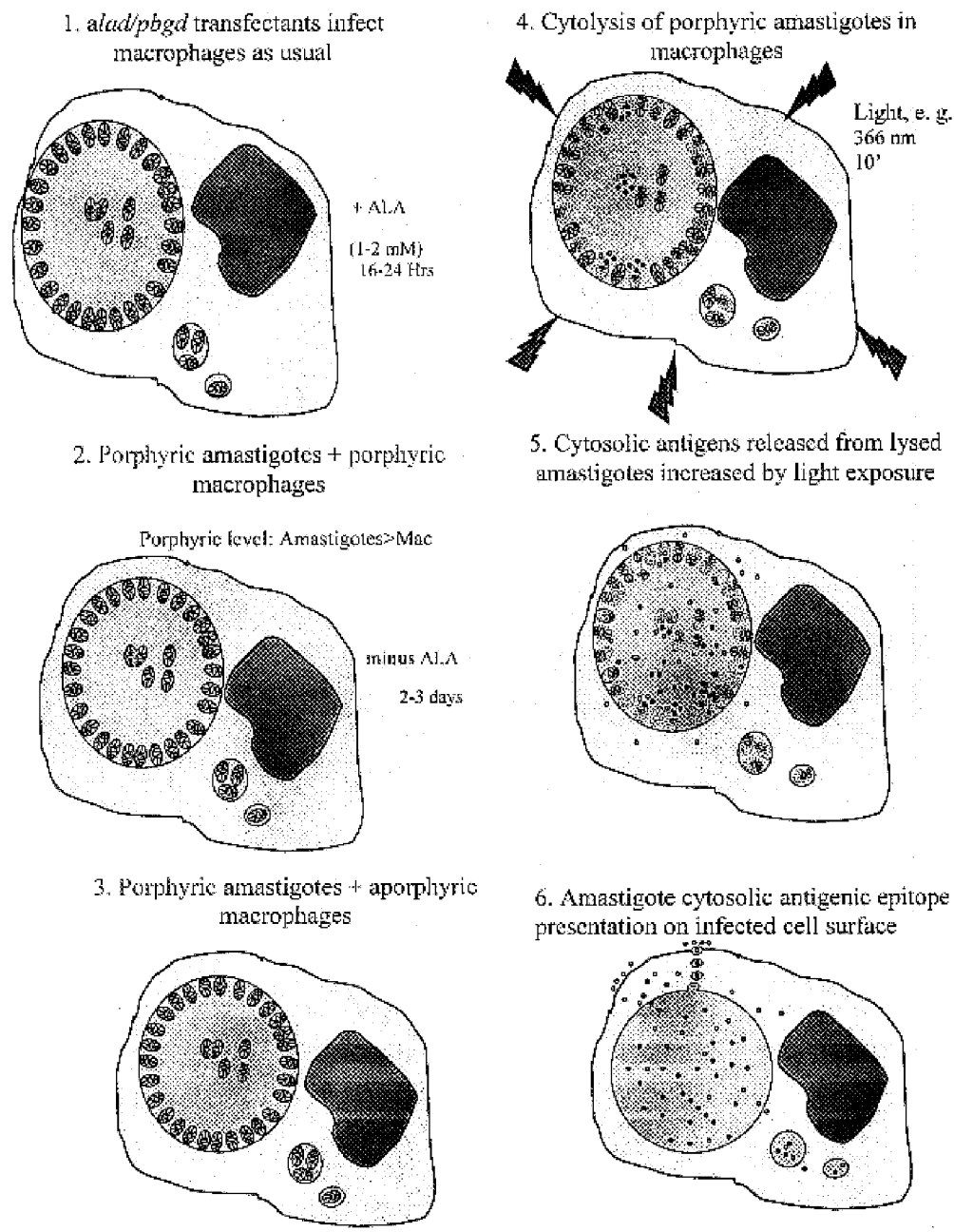
FIG. 16 is a diagrammatic depiction of porphyric *Leishmania* for developing live vaccine model as ALA-inducible and light-controllable suicidal mutants.

We have carried out approximately 20 independent experiments to obtain the optimal experimental conditions, by which uroporphyria of intracellular amastigotes is maximized with minimal porphyria of the macrophages or their host cells. Application of this scheme for proposed use as a live vaccine model is depicted in FIG. 16.

EXAMPLE 10

Reduced Pathogenicity and Vaccination by Suicidal *Leishmania* Mutants in Various Animal Models and Immunoprophylatic Effects in Hamster Model for Kala-azar Evidence from in vivo studies indicates that the pathogenicity of *L. amazonensis* alad/pbgd double transfectants is significantly reduced when rendered uroporphyric either before or after inoculation into a variety of different animal models. The lesions produced by porphyric *Leishmania* develop more slowly or contain fewer amastigotes or are smaller in size when compared against the controls. There is also preliminary evidence, suggestive of differences in immune responses between the experimental and control groups.

Figure 18:
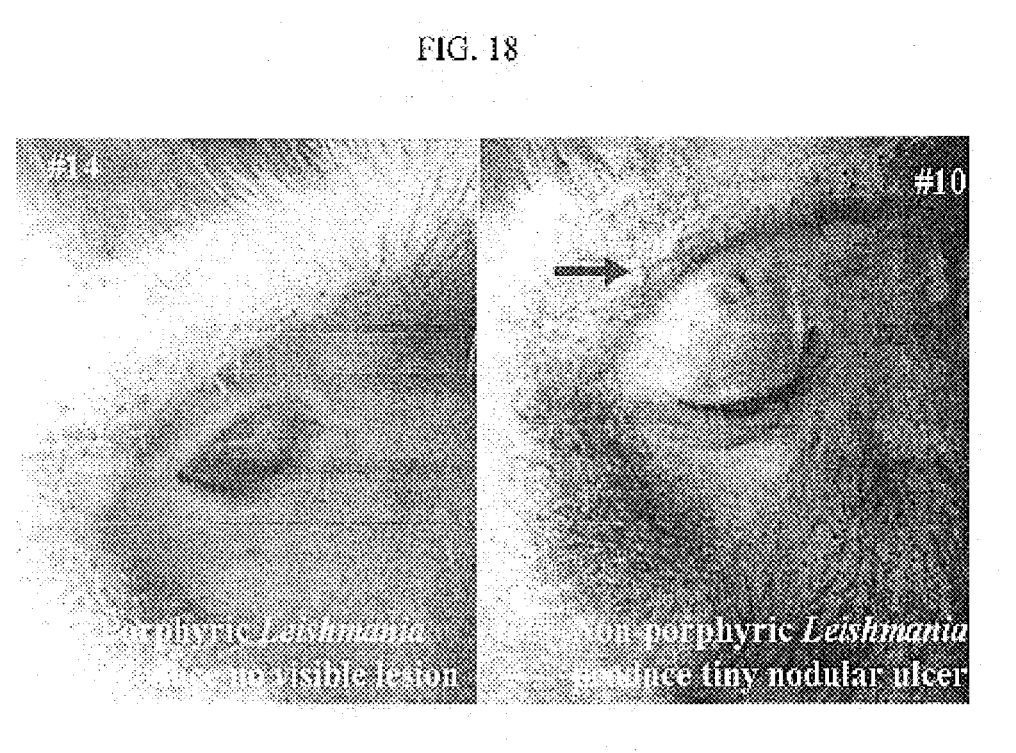
Figure 19:
Figure 20:
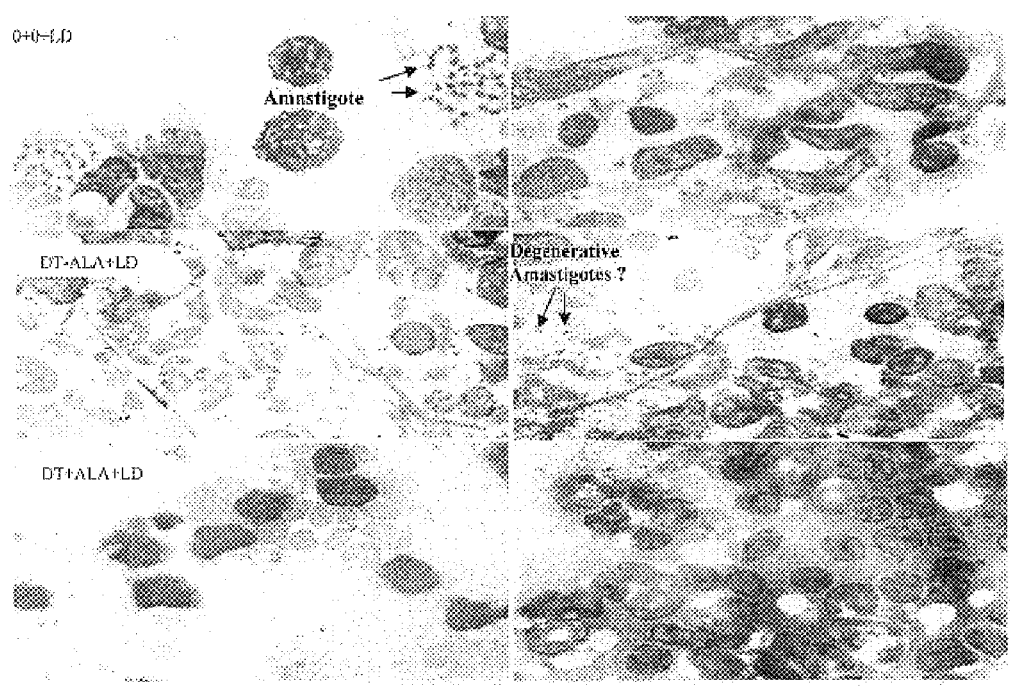
Figure 21:
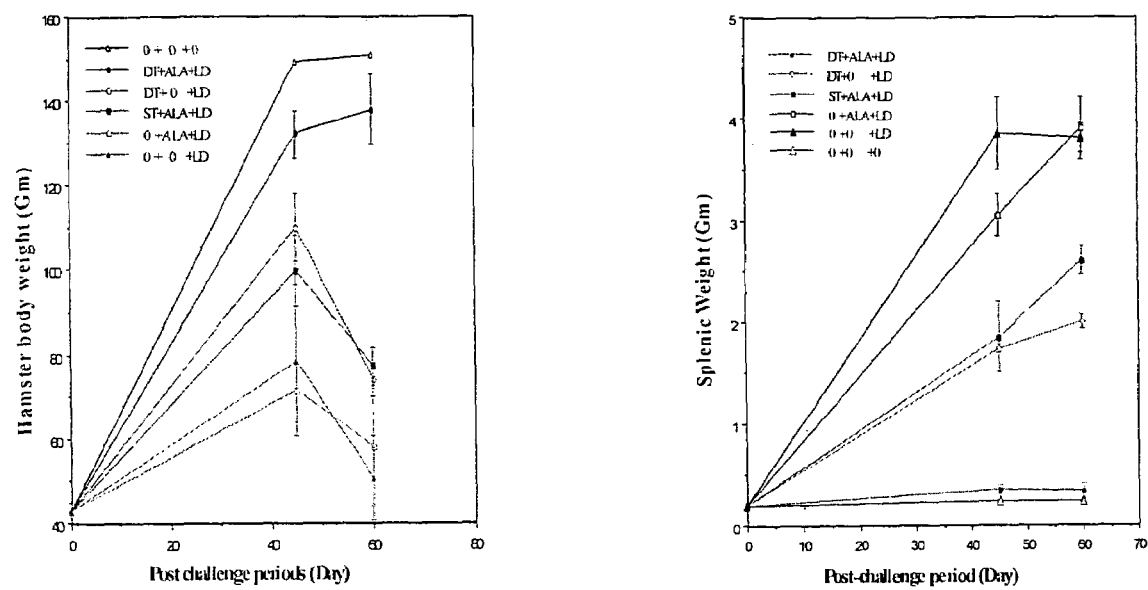
Figure 23:
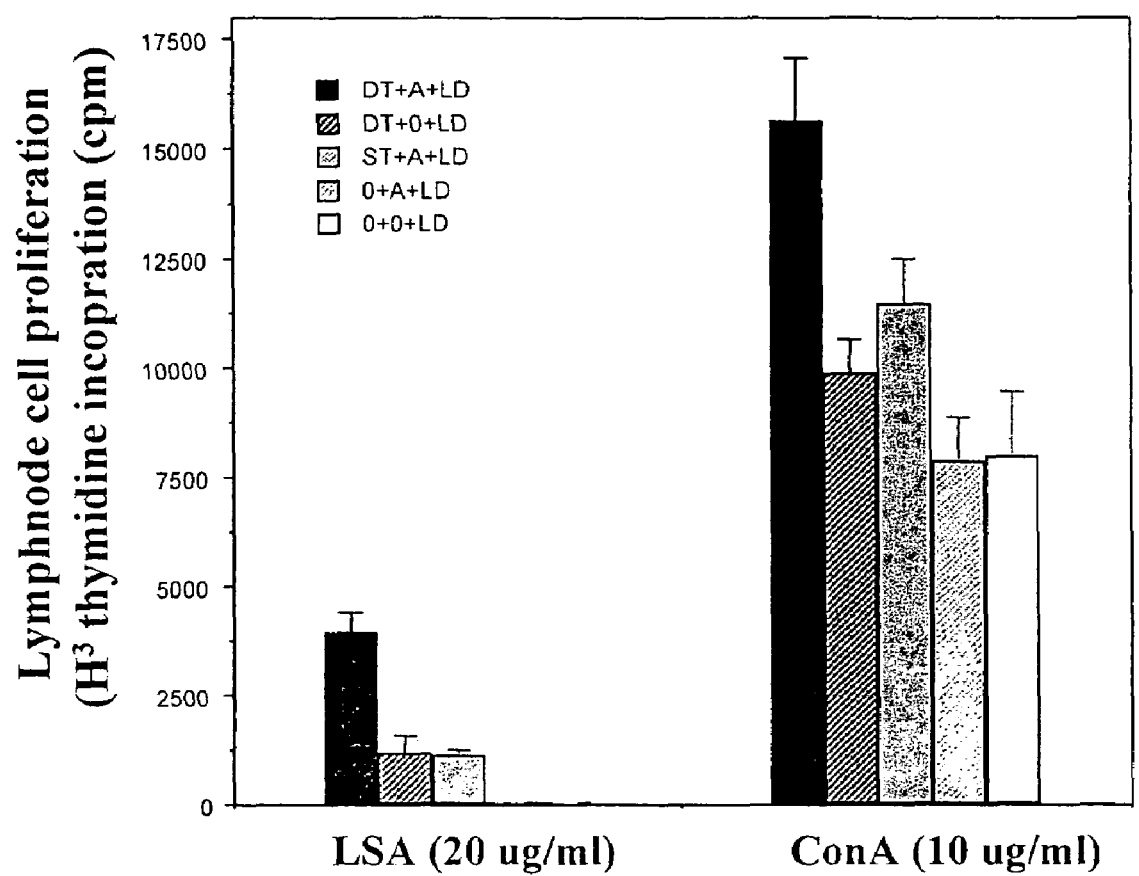

These studies have been undertaken using the following protocols provided on the basis of in vitro studies already presented (FIGS. 18-20).

Protocol 1—In vivo Induction of Uroporphyria After Animal Inoculation

1. Day 0: Inoculate stock transfectants from drug-containing to drug-free medium (1-2×10$^6$ cells/ml). Grow transfectants for one cycle in drug-free medium to avoid drug transfer to animals.

2. Day 2-7: Grow cells to stationary phase (=50×10$^6$/ml) after incubation in transit and after arrival. Full turbidity at this growth phase is reached in 5-7 days.

3. Day 7: Inoculate 3 groups of 5-10 animals, each with 10$^6$ and/or 10$^7$ cells:
   Group 1: DT+ALA+Light—Porphyric-double transfectants for ALA treatment+light illumination
   Group 2: DT+0+Light—Aporphyric-double transfectants for PBS or HBSS controls
   Group 3: ST+ALA+Light—Aporphyric-single transfectants control for ALA treatment+light 4. ~Day 9-12: Inject 100 mM ALA solution, ~2 days after inoculation, to the same site daily for 4 times for the experimental groups. Controls receive PBS or HBSS. Volumes for different sites are: Footpad, ~25 ul; Tail-base, 100 ul.

5. ~Day 13-17: Illuminate for 4 days the caged animals daily with regular white light or at red range of 600-700 nm wavelengths using: [1] Red light bulb (50-100 W) 1-2 feet above caged animals for regular periodicity, e.g., 8 AM-6 PM. The light source is placed at the shortest distance above the cage without raising normal ambient temperatures of the animals; or [2] Transparent red paper wrapping around all sides of animal cages (when there are other on-going experiments in the same room). Porphyrins are excitable by a wide spectrum of wavelengths. Red light is chosen because it is known to penetrate deep into the dermis (Harth et al. 1998; Lane, 2003).

6. ~Day 17-30 or longer: Measure lesion size weekly and/or assess parasite burdens in lesion homogenates microscopically or by limiting dilution method. Evaluate immunological differences between experimental and control groups using immune cells from the sites of inoculation and their draining lymph nodes.

7. ~Day 15-30: Challenge the remaining animals at a different site with *Leishmania* species of local interests. Conditions for challenging and evaluation vary with species, previous experiences and conditions.

Protocol 2—In Vitro Induction of Uroporphyria Before Animal Inoculation

Inoculation of animals with double transfectants already rendered porphyric in vitro avoids tedious and potentially deleterious multiple injections for large animals (monkeys), as prescribed in the 1$^{st}$ protocol. It also simplifies the experiments by using only double transfectants.

1. Day 0: Prepare porphyric and control double transfectants in culture:
   [1] DT+0 (Control): 10$^8$ promastigotes/ml in HBSS-HEPES (pH 7.4)+0.01% BSA
   [2] DT+ALA (Experimental): Porphyric: Same as above, but 1 mM ALA added
   Incubate at ~25° C. in darkness for developing uroporphyria 2. Day 2: Inoculate 3 groups of 5-10 animals, each with 10$^7$ cells/animal when cell porphyria reaches optimum in [2]:
   Group 1 with DT+0 cells [1] as non-porphyric control
   Group 2 with DT+ALA cells [2] porphyria+red light illumination
   Group 3 with DT+ALA cells [2] porphyria+regular light illumination 4. ~Day 3-6: Illuminate the caged animals daily for 4 days, as in Protocol 1.

6. ~Day 7-21 and beyond: Evaluate the results, challenge (days 14-21) and follow-up in Protocol I.

Mouse Tailbase Models

In mouse tailbase models using Protocol 1, porphyric double transfectants were found to produce lesions much smaller than aporphyric single transfectants. Both experimental (porphyric double transfectants) and control groups (aporphyric single transfectants) were treated identically according to Protocol 1. Only the former develops uroporphyria. The difference between the experimental and control groups in lesion development was already obvious 21 days post-inoculation and became more pronounced upon further incubation for 48 days (Lesion size: 358±56 mm for non-porphyric single transfectants versus 203±67 mm for double transfectants). This is more obvious in AJ mice than in BALB/c mice (FIG. 17). BALB/c mice of the experimental group, but not those of the control group, appear to be more resistant against homologous challenges at the footpad (Not shown). Heterologous challenges of the AJ mice with *T. cruzi* produced identical parasitemia of this trypanosome in both experimental and control groups, indicative of no cross-genus protective immunity, as expected. Further studies include transfection of porphyric *Leishmania* with *T. cruzi* vaccine candidates.

Vervet or African Green Monkey Model

In Vervet or African green monkey model using Protocol 2, ALA-treated double transfectants were found to produce no lesion in the eyebrow ridge 2 weeks after inoculation (FIG. 18), Primate Research Institute, Nairobi. Small lesions developed in the control groups (FIG. 18), consisting of double transfectants without ALA treatments and single transfectants with ALA treatments. Measurements of the lesions from 5 monkeys for each group revealed that they are twice larger in the control groups than the experimental group (Table 4).

TABLE 4

Porphyria of *L. amazonensis* reduces its lesion development in vervet monkey

| Transfectant | +1 mM ALA | Monkey # inoculated | Lesion size (mm) 9 day | 16 day |
|---|---|---|---|---|
| pbgd/alad | Uroporphyria | 5 | 5.7 ± 1.7 | 06.1 ± 1.1 |
| pbgd/alad | none | 5 | 8.1 ± 5.9 | 13.1 ± 7.3 |
| pbgd/pX | none | 5 | N/D | 13.5 ± 7.8 |

Suicidal Cytolytic Delivery of *L. Amazonensis* Protects Syrian Golden Hamsters Against Experimental Visceral Leishmaniasis (Indian kala-azar) caused by *L. donovani* DD8.

In two separate experiments, immunoprophylatic activities were noted with induced cytolytic porphyric *L. amazonensis* according to Protocol 1 against visceral leishmaniasis in Syrian Golden hamsters. It is the best model, since it closely mimics this disease in clinical manifestations of patients, including cachexia/body weight loss, immunosuppression, splenomegaly and fatal consequence.

Minor modifications were introduced in the 2$^{nd}$ Experiment for improvement according the experiences of the 1$^{st}$ Experiment. In Experiment 1, hamsters were vaccinated at the footpads and exposed to red light after ALA treatment to induce specific uroporphyia of intracellular transgenic *Leishmania*. In Experiment 2, hamsters were vaccinated at the back on shaved areas to facilitate their exposure to illumination from the top and were exposed to white light, which proved effective in separate in vitro studies. Both experiments were described in some details below.

EXPERIMENT 1

Day 00—Feb. 23, 2004: Culture 3×4 ml alad/pbgd double transfectants (DT) (1 drop=~2×10$^6$/ml) Day 03—Feb. 23-27, 2004: Transit for 3 days to destination laboratory Day 07—Feb. 23-27, 2004: Cell count=24×10$^6$/ml (80% active motile promastigotes)

Day 10—Mar. 4, 2004: Inoculate 25 hamsters (40-45 gm) at 38×10$^6$/hamster footpad Day 14—Mar. 8-11, 2004: Inject inoculation site with 4×30 ul 1 mM ALA daily for 4 days Day 18—Mar. 12, 2004: Illuminate caged hamsters in 2 ft×3 ft×2 ft thermocol perforated box under board-mounted red light: 30' 6 bulbs 15 W Phillips & 30' 2 bulbs 5 hrs later.

Group 1. DT+ALA=5 (minus 5 died during light treatment)

Group 2. DT−ALA=10

Group 3. Unvaccinated control=10

Day 31—Mar. 25, 2004: Challenge all intracardially 10$^7$*L. donovani* DD8 amastigotes (LD)/0.1 ml/animal. 2 wks post-vaccination: (no lesions at the vaccination sites).

Day 78—May 11, 2004: (47 days post-challenge) Sacrifice animals for evaluations

Group 1. DT+ALA+LD (porphyric experimental)

Group 2. DT−ALA+LD (non-porphyric control)

Group 3. 0+0+LD (Unvaccinated control)

Results: Notable during the course of the observations for about 2 months after challenging infection is the difference in body weight between experimental and control groups. At the termination of the experiments, hamsters of the experimental group 1 appeared active, healthy and increased in body weight from ~40 gm to ~135 gm (FIG. 19 DT+ALA+LD), whereas those of the unvaccinated control groups were lethargic, suffered from cachexia and weighed only ~90 gm (FIG. 19 0+0+LD). The latter signs are typical to the terminal stage of kala-azar in this animal model. This is indicated by microscopic examinations of splenic impression smears after Geimsa staining for parasite burdens or Id loads. Amastigotes appeared normal and abundant in unvaccinated control group (FIG. 20, 0+0+LD) and, albeit less well-defined, in the non-porphyric control group (DT+0+LD), but were extremely sparse in the porphyric experimental group (DT+ALA+LD). Enumeration of amastigote number per 1,000 splenic nuclei showed a difference by 9-10 fold in parasite loads between the experimental and control groups (Table 5). The results from the 1$^{st}$ preliminary experiments are thus encouraging, suggestive of immunoprophylatic activities of the transgenic mutants after their cytolysis in vivo induced by ALA and light.

TABLE 5

Vaccination of hamsters with suicidal porphyric *Leishmania amazonensis* mutants protects them against challenges by visceralizing *Leishmania donovani*.

| Group | Vaccination | Hamster No. | *Parasite burdens |
|---|---|---|---|
| 1 | DT + ALA | 5 | 103 ± 09.23 |
| 2 | DT − ALA | 10 | 852 ± 19.5 |
| 3 | Unvaccinated control | 10 | 950 ± 22.7 |

Note:
~10 fold reduction of parasite loads in vaccinated group 1 vs control groups 2–3 two months after challenges.
*No of amastigotes/1000 splenic cell nuclei (Mean value ± SD)

EXPERIMENT 2

The 2$^{nd}$ experiment was designed to verify and to strengthen the results of the 1$^{st}$ experiment by including 2 additional control groups. One is to treat animals with ALA alone so as to eliminate the potential contribution of this metabolite to the outcome observed. Another is to include pbgd single transfectants (ST) as an additional non-porphyric control to ascertain that the prophylactic effects observed are independent of factors specific to DT or *L. amazonensis* infection alone. There is some indication of this in the 1$^{st}$ experiment for "vaccination" of hamsters with the DT−ALA+LD group whose splenic parasite loads remained high, but the amastigotes look degenerative (FIG. 20). Except for "vaccination" on the back and illumination with white light, experimental conditions otherwise followed those in the 1$^{st}$ as follows:

A total of 50 Syrian Golden hamsters (40-45 gm) were used 10 per group for each of the following experimental and control groups:

Group 1. Double transfectants DT+ALA

Group 2. DT alone without ALA DT−ALA

Group 3. Single transfectants ST+ALA

Group 4. ALA treatment alone 0+ALA
Group 5 Unvaccinated control 0+0
Day 0 (Sep. 22, 2004): Ship cells inoculated into four flasks under non-selective conditions
Day 3 (Sep. 25, 2004): Reach destination laboratory
Day 4 (Sep. 26, 2004): Add 2 ml fresh medium to each flask.
Day 6 (Sep. 28, 2004): Harvest and resuspend cells for inoculation intradermally to a shaved area (~2 cm×2 cm) on the back of the animals as follows:
(A) DT: $3 \times 10^8$ cells/1.1 ml to 20 hamsters at ~$1.5 \times 10^7$ cells/50 ul each
(B) ST: $10^8$ cells/0.6 ml to 10 hamsters at ~$10^7$ cells of 50 ul each
Days 6-9 (Sep. 28-Oct. 1, 2004): Allow *Leishmania* to establish infection in macrophages
Days 9-12 (Oct. 1-4, 2004): inject the same site of each animal daily 4× with 20 ul 100 m ALA solution Days 13-17 (Oct. 5-9, 2004): Illuminate caged animals from 9 AM to 5 PM daily for five days under white light [Four bulbs of 100 W (Phillips)+2 tube lights of 40 W in an AC room of 6 ft×6 ft×10 ft] 2 ft above, keeping a constant temperature of 26-27° C.

Day 31 (Oct. 25, 2004): Challenge 9 animals of each group with 107 DD8 strain of *L. donovani* amastigotes/animal by intracardiac route.

Day 78 (Dec. 9, 2004): Parasitological/immunological evaluations-45 days post-challenge (FIG.).

Day 93 (Dec. 24, 2004): Parasitological/immunological evaluations-60 days post-challenge (FIG.).

Day 147 (Feb. 16, 2005): survivors left of a total of 4 animals 114 days after challenge, excluding 6 sacrificed for experimentation on days 0, 45, and 60.

4/4 Group 1. Double transfectants DT+ALA+LD (porphyric experimental)

2/4 Group 2. DT alone without ALA DT−ALA+LD (non-porphyryic control 2)

2/4 Group 3. Single transfectants ST+ALA+LD (non-porphyric control 2)

0/4 Group 4. ALA treatment alone O+ALA+LD (ALA control 1)

0/4 Group 5 Unvaccinated control 0+0+LD (non-vaccinated control 3)

Results obtained from the $2^{nd}$ experiment substantiated those of the $1^{st}$ when assessed on days 45 and 60 post-challenging infection. The porphyric experimental group (FIG. 21, left Panel, DT+ALA+LD) gains weight by 3-4 folds, approaching that of the normal untreated and uninfected hamsters (0+0+0). This is in sharp contrast to the changes of the 2 non-porphyric control groups in weight, which increases initially by 2-2.5 folds on day 45 followed by a sharp decrease on day 60 (FIG. 21 Left Panel, DT−ALA+LD; ST+ALA+LD). These 2 groups, however, lost weight more slowly than ALA control groups (FIG. 21 Left Panel. 0+ALA+LD), which is virtually identical to non-vaccinated group (0+0+LD). Splenomegaly of different groups determined by weights is completely consistent with the body weight data, but in reverse of the actual readings, as expected. Namely, splenomegaly is marginal in porphyric experimental group (FIG. 21 Right Panel DT+ALA+LD) comparable to untreated and uninfected normal hamsters (0+0+0) and is most pronounced in ALA control group (0+ALA+LD) almost identical to non-vaccinated and infected group (0+0+LD). Here again, in between these two extremes of splenomegaly are the 2 non-porphyric groups (FIG. 21, Right Panel DT−ALA+LD, St+ALA−LD).

Assessments of splenic parasite loads also yielded a similar, but more dramatic picture in favor of the porphyric cytolytic mutants as prophylatically most effective. In this group, amastigotes are hard to find in splenic impression smears apparently due to a precipitous decrease in number from day 45 to day 60 post challenge infection (FIG. 22 Left and Right Panels, DT+ALA+LD). In all 4 control groups (DT−ALA+LD, ST+ALA+LD, 0+ALA+LD and 0+0+LD), amastigotes are microscopically visible readily (Left Panel) and abundant in number (Right Panel), although a slight difference in their number is still discernable between the non-porphyric groups (DT−ALA+LD; ST−ALA+LD) and the other control groups without *L. amazonensis* infection (0+ALA+LD; 0+0+LD).

The lymph node cells from DT+ALA+LD mounted the strongest immune response over all the control groups to T-cell mitogen (Con-A) and to *Leishmania* soluble antigens (LSA) (FIG. 23). The response as assessed by tritiated thymidine incorporation segregated them into the expected order of: DT+ALA+LD>DT-ALA+LD=ST+ALA+LD>0+ALA+LD=0+0+LD, consistent with the data presented in FIGS. 21-22. The response of all groups to Con-A is higher than to LSA. This is not unexpected, since the former is a non-specific T-cell mitogen. Of particular interest is the specificity of LSA, which elicits virtually no response of the 2 controls without *L. amazonensis* (0+ALA+LD; 0+O+LD) and a modest response of the 2 non-porphyric controls (DT−ALA+LD; ST+ALA+LD). This suggests that antigen-specific immune response is suppressed by *L. donovani* infection, which is modestly reversed by pre-infection with transgenic *L. amazonensis* under non-porphyric conditions. Significantly, this specific immune response is enhanced by several folds only when the latter is exposed to ALA and light to induce their uroporphyria followed by intracellular cytolysis.

Significantly, DT+ALA+light produced no cutaneous lesions at the site of inoculation during the entire course of the present investigation in both experiments 1 and 2. In contrast, cutaneous lesions of 0.3 to 0.4 cm in diameter did develop at the site of inoculation when using the non-porphyric controls, e.g., DT−ALA+light. This observation strongly indicates that intracellular DT were either lysed completely or reduced to an insignificant number insufficient to cause cutaneous leishmaniasis. The scheme of "vaccination" by using these suicidal mutants thus not only elicit immunoprophylatic effects against *L. donovani* but also, at the same time, commit self-destruction to a desirable outcome.

Taken together, the results serve to illustrate the following points: [1] ALA alone is ineffective and probably cause no more than a transient porphyria at the site of injection; [2*]* *L. amazonensis* infection alone appears to delay the onset of visceral leishmaniasis in this model, but the effect is transient and marginal; and [3] only the double transfectants induced to undergo intracellular cytolysis produces an immunoprophylactic effect under the experimental conditions used; [4] this protective phenotype appears to be antigen-specific, as indicated by a selective increase of the experimental group in their immune response to LSA; and [5] finally, the suicidal mutants appear to have an excellent safety margin for use as a live vaccine, since they produce no lesions at the site of inoculation when exposed to ALA, which is known from in vitro observations to induce porphyria sensitive to light for cytolysis.

EXAMPLE 11

Construction of Additional Porphyric Leishmania Suicidal Mutants to Optimize their Potential Use as an Effective Live Vaccine Model It is contemplated that additional porphyric suicidal mutants can be prepared from different Leishmania species selected from our available stocks with a spectrum of pathogenicity, ranging from totally avirulent to highly virulent ones. We can use L. tarentolae as a representative of the avirulent species, since it was originally isolated from cold-blooded reptiles, i.e., lizards. Members of this species are thus not expected to survive in warm-blooded mammalian hosts, like humans. However, this species when grown as promastigotes retain their ability to infect macrophages in vitro, although they fail to replicate intracellularly and eventually perish in these phagocytes. Some insect trypanosomes have been observed also to survive in these cells for an extended period in vitro (Rozental et al., 1987). Similar flagellated protozoa were recovered even from AIDS patients (Chicharro and Alvar, 2003; Gramiccia et al., 1992; Pacheco et al., 1998), but they have not been proven as disease-causing opportunists in these immunocompromised subjects. Lizard Leishmania and the like thus appear to retain some infectivity for homing vaccines to antigen presenting cells, but their short intralysosomal survival in these cells may render antigen processing inefficient. Clearly, this is a trade off against their greater margin of safety by being avirulent or least virulent. We can eliminate any lingering concerns of their residual pathogenicity, if there should be any, by rendering them porphyric for suicidal cytolysis via transgenetic manipulations. We can also prepare such mutants for those at the other end of the spectrum of pathogenicity, e.g., members of L. donovani and L. infantum, which cause potentially fatal human visceral diseases. These species infect cultured macrophages readily and undergo several rounds of intralysosomal replication, especially when amastigotes are used. Different strains of these species produce visceral leishmaniasis in hamster and dog. The invasiveness of these species is an integral part of their virulence, but the molecular determinants of relevance to "infection" do not themselves cause the "disease" per se (Chang et al., 2003). Instead, they let these parasites sneak into macrophages. The utility of infectious species facilitates not only the homing of vaccines into antigen-presenting cells but also effective antigen processing due to their intralysosomal persistence. We can genetic engineer these virulent species for porphyria to selectively harness these favorable traits. Such transfectants are allowed to proceed with the infection as usual first. Then, they are timely signaled externally to commit suicide intralysosomally, thereby releasing vaccines in the desirable site. We further can evaluate Leishmania spp. intermediate between these two at the extreme ends of the pathogenicity spectrum. The ideal live vaccine models for our suicidal design are among those, which retain optimal infectivity with minimal pathogenicity. Priority is to be given to L. major, which is mildly pathogenic by causing self-healing simple cutaneous leishmaniasis. Moreover, it has been used successfully as live virulent vaccines for "Leishmanization" in human immunization programs (see Introduction). In addition, we can use L. turanica and L. gerbilli, which are phylogenetically closely related to L. major, but they are gerbil parasites and cause little or no diseases in humans. We can include L. enriettii, which is a parasite of guinea pig, although its origin is somewhat ambiguous as well as L. tropica causing anthroponotic cutaneous leishmaniasis.

We have produced uroporphyric mutants and already obtained uroporphyric L. major. A full set of alad and/or pbgd single and double transfectants of this species is available (Table 2). Only the double transfectants become uroporphyric when exposed to ALA, as expected. We have also transfected some of the other aforementioned species, e.g., L. infantum, L. donovani and L. enrietii. We can continue this by using the same plasmid constructs available (Sah et al., 2002) in conjunction with multiple isolates for the same genotype or species (FIG. 1). This approach ensures us not only the successful transfection, but also offer us the selection of those with best biological properties, e.g., in vitro growth as promastigotes, infection of macrophages, and in vivo infectivity. There are several ways to improve Leishmania infectivity, which is lost either naturally or in the laboratory. Infectivity of L. torentolae and the like are expected to increase after transfection of this species (Tamar et al., 2000) with invasive/evasive determinants (Chang et al., 2003) identified from pathogenic species. Clinical isolates of pathogenic species from patients are known to lose their infectiveness after in vitro cultivation as promastigotes. This is recoverable by recycling of these isolates repeatedly via in vitro infection of macrophages and/or in susceptible animals. Such manipulations can be applied to recover infectivity from those, which may lose this ability due to a prolonged period of in vitro selection for transfectants. Transfectants obtained can be assessed as before for the presence of PBGD and ALAD for their enzyme activities and for the development of uroporphyria in response to ALA fluorometrically by TLC and by fluorescent microscopy as promastigotes, axenic amastigotes, in-macrophage amastigotes and those from infected animals where feasible. Methodology for these are published (Anderson et al., 1978; Kappas et al., 1969; Sassa, 1982; Sassa et al., 1974) and detailed in the legends to Tables 1-3 and FIGS. 10-15. In addition, the sensitivity of intracellular and extracellular porphyric cells to illumination at different wavelengths will be assessed under different conditions to provide baseline levels for work in animal models. We expect to have additional transfectants available from different species/ strains and fully characterized experimentally.

In addition, we can produce coproporphyric Leishmania spp. Coproporphyrins are relatively hydrophobic and thus tend to become membrane-associated, accounting for their greater retention by cells. This is in contrast to the release of hydrophilic uroporphyrins from porphyric cells. Leishmania accumulation of coproporphyrins in response to ALA thus will significantly enhance porphyria-mediated cytolysis of the suicidal mutants. Such mutants can be created by additional transfection of alad/pbgd double transfectants with urod, which encodes uroporphyrinogen decarboxylase (UROD)—the $5^{th}$ enzyme in the heme biosynthesis pathway (FIG. 2). UROD catalyzes the formation of coproporphyrin I as a metabolically dead-end product from uroporphyrin I in the absence of uroporphyrinogen co-synthase (Chartrand et al., 1979). We can engineer such mutants in two principal ways. The simplest way is to clone urod into a $3^{rd}$ vector using a selectable marker other than neo and nagt, which are already used with pX and p6.5 vectors for episomal expression of alad and pbgd in the double transfectants. The $3^{rd}$ vector can include genes resistant to one of the following antibiotics: hygromycin, bleomycin, puromycin, blasticidin-S or nourseothricin in Leishmania-specific vectors of the pXG series. We have already used urod in pXg-hyg for successful transfection of wildtype, single (alad) and double (alad/pbgd) transfectants of *L. amazonensis*. Simultaneous transfection of wildtype with all three vectors carrying these genes also produced triple drug-resistant mutants. These results point to the ease of such genetic engineering. We can also produce porphyric *Leishmania* by a different way using pIR—1SAT (Joshi et al., 1995) construct, also from S M Beverley. It consists of 2 independent expression sites flanked by ~1 kb flanking sequences of the ssurRNA gene for Pol I-promoter site-specific chromosomal integration via homologous recombination. Chromosomal integration of alad and pbgd is expected to result in their stable expression in the mutants and thus development of uroporphyria is expected in the absence of selective pressure. Episomal transfection of these knock-in mutants with urod is further expected to produce coproporphyrin I. The levels of this porphyrin will be controllable more readily in such mutants by raising the selective pressure for urod.

It is understood that, given the above description of the embodiments of the invention, various modifications may be made by one skilled in the art. Such modifications are intended to be encompassed by the claims below.

REFERENCES

Abels C, Fritsch C, Bolsen K, Szeimies R M, Ruzicka T, Goerz G, Goetz A E. Photodynamic therapy with 5-aminolaevulinic acid-induced porphyrins of an amelanotic melanoma in vivo. Journal of Photochemistry and Photobiology, B. 1997 August; 40(1):76-83.

Afonso S G, Chinarro S, Munoz J J, de Salamanca R E, Batlle A M. Photodynamic and non-photodynamic action of several porphyrins on the activity of some heme-enzymes. Journal of Enzyme Inhibitors. 1990; 3(4):303-10.

Ahmed S B, Bahloul C, Robbana C, Askri S, Dellagi K. A comparative evaluation of different DNA vaccine candidates against experimental murine leishmaniasis due to *Leishmania major*. Vaccine. 2004; 22:1631-9.

Akman L, Aksu H S, Wang R Q, Ozensoy S, Ozbel Y, Alkan Z, Ozcel M A, Culha G, Ozcan K, Uzun S, Memisoglu H R, Chang K P. Multi-site DNA polymorphism analyses of *Leishmania* isolates define their genotypes predicting clinical epidemiology of leishmaniasis in a specific region. J Eukaryot Microbiol. 2000; 47:545-54.

Alexander J, Coombs G H, Mottram J C. *Leishmania mexicana* cysteine proteinase-deficient mutants have attenuated virulence for mice and potentiate a Th1 response. J. Immunol. 1998; 161:6794-801.

Anderson W L, Shechter Y, Parikh I. Quantitation of methionyl peptides in nanomole quantities by a fluorometric method. Anal Biochem. 1978; 91:481-9.

Belkaid, Y., H. Jouin and G. Milon (1996). "A method to recover, enumerate and identify lymphomyeloid cells present in an inflammatory dermal site: a study in laboratory mice." J Immunol Methods 199(1): 5-25.

Belkaid Y, Kamhawi S, Modi G, Valenzuela J, Noben-Trauth N, Rowton E, Ribeiro J, Sacks D L. Development of a natural model of cutaneous leishmaniasis: powerful effects of vector saliva and saliva preexposure on the long-term outcome of *Leishmania major* infection in the mouse ear dermis. J Exp Med. 1998; 188:1941-53.

Bissonnette R, Tremblay J F, Juzenas P, Boushira M, Lui H. Systemic photodynamic therapy with aminolevulinic acid induces apoptosis in lesional T lymphocytes of psoriatic plaques. Journal of Investigative Dermatology. 2002 July; 119(1):77-83.

Burchmore R J, Rodriguez-Contreras D, McBride K, Merkel P, Barrett M P, Modi G, Sacks D, Landfear S M. Genetic characterization of glucose transporter function in *Leishmania mexicana*. Proc Natl Acad Sci USA. 2003; 100:3901-6.

Campbell K, Diao H, Ji J, Soong L. DNA immunization with the gene encoding P4 nuclease of *Leishmania amazonensis* protects mice against cutaneous Leishmaniasis. Infect Immun. 2003; 71:6270-8.

Campbell K, Popov V, Soong L. Identification and molecular characterization of a gene encoding a protective *Leishmania amazonesis* Trp-Asp (WD) protein. Infect Immun. 2004; 72:2194-202.

Castro D J, Saxton R E, Soudant J. The concept of laser phototherapy. Otolaryngolical Clinic of North America. 1996 December;29(6):1011-29.

Chang K P. Human cutaneous Leishmanias in a mouse macrophage line: propagation and isolation of intracellular parasites. Science. 1980; 209:1240-42.

Chang K P. Intracellular multiplication of *Leishmania donovani* during repeated passages in primary cultures of hamster peritoneal macrophages. J Parasitol. 1978; 64:931-3.

Chang K P, Akman L, Nielsen J S. *Leishmania* virulence and genetic heterogeneity. Clinical Dermatology. 1999 May-June; 17(3):269-73.

Chang K P, Chang C S, Sassa S. Heme biosynthesis in bacterium-protozoon symbioses: enzymic defects in host hemoflagellates and complemental role of their intracellular symbiotes. Proc Natl Acad Sci USA. 1975; 72:2979-83.

Chang K P, Dwyer D M. Multiplication of a human parasite (*Leishmania donovani*) in phagolysosomes of hamster macrophages in vitro. Science. 1976; 193:678-80.

Chang K P, Hendricks D L. Laboratory cultivation and maintenance of *Leishmania* In: Human Parasitic Diseases. Vol 1, Leishmaniasis (Chang K.-P. and Bray R S, eds). 1985; Elsevier, Amsterdam. pp. 213-46.

Chang K P, Reed S G, McGwire B S, Soong L. *Leishmania* model for microbial virulence: the relevance of parasite multiplication and pathoantigenicity. Acta Trop. 2003; 85:375-90.

Chang K P, Trager W. Nutritional significance of symbiotic bacteria in two species of hemoflagellates. Science. 1974; 183:531-2.

Chakrabarty R, Mukherjee S, Lu H G, McGwire B S, Chang K P, Basu M K. Kinetics of entry of virulent and avirulent strains of *Leishmania donovani* into macrophages: a possible role of virulence molecules (gp63 and LPG). Journal of Parasitology. 1996 August;82(4):632-5.

Chartrand P, Tardif D, Sasarman A. Uroporphyrin- and coproporphyrin I-accumulating mutant of *Escherichia coli* K12. J Gen Microbiol. 1979; 110:61-6.

Chen D Q, Kolli B K, Yadava N, Lu H G, Gilman-Sachs A, Peterson D A, Chang K P, Episomal expression of specific sense and antisense mRNAs in *Leishmania amazonensis*: modulation of gp63 level in promastigotes and their infection of macrophages in vitro. Infect Immun. 2000; 68:80-6.

Chen D Q, Lu H, Chang K P. Replacement of *Leishmania* N-acetylglucosamine-1-phosphate transferase gene requires episomal rescue. Mol Biochem Parasitol. 1999; 100:223-7.

Chicharro C, Alvar J. Lower trypanosomatids in HIV/AIDS patients. Ann Trop Med Parasitol. 2003; 97 Suppl. 1:75-8.

Coler R N, Skeiky Y A, Bernards K, Greeson K, Carter D, Cornellison C D, Modabber F, Campos-Neto A, Reed S G. Immunization with a polyprotein vaccine consisting of the T-Cell antigens thiol-specific antioxidant, *Leishmania major* stress-inducible protein 1, and *Leishmania* elongation initiation factor protects against leishmaniasis. Infect Immun. 2002; 70:4215-25.

Cruz A, Coburn C M, Beverley S M. Double targeted gene replacement for creating null mutants. Proc Natl Acad Sci USA. 1991; 88:7170-4.

Du Y, Maslov D A, Chang K P. Monophyletic origin of beta-division proteobacterial endosymbionts and their coevolution with insect trypanosomatid protozoa Blastocrithidia culicis and *Crithidia* spp. Proceedings of the National Academy of Science USA. 1994 Aug. 30;91(18):8437-41.

Edgeworth R L, San J H, Rosenzweig J A, Nguyen N L, Boyer J D, Ugen K E. Vaccine development against HIV-1: current perspectives and future directions. Immunology Res. 2002;25(1):53-74.

Etges R, Muller I. Progressive disease or protective immunity to *Leishmania major* infection: the result of a network of stimulatory and inhibitory interactions. J Mol Med. 1998; 76:372-90.

Freedman D J, Beverley S M. Two more independent selectable markers for stable transfection of *Leishmania*. Mol Biochem Parasitol. 1993; 62:37-44.

Friesen S A, Hjortland G O, Madsen S J, Hirschberg H, Engebraten O, Nesland J M, Peng Q. 5-Aminolevulinic acid-based photodynamic detection and therapy of brain tumors (Review). International Journal of Oncology. 2002 September;21(3):577-82.

Gibson S L, Havens J J, Nguyen M L, Hilf R. Delta-aminolaevulinic acid-induced photodynamic therapy inhibits protoporphyrin IX biosynthesis and reduces subsequent treatment efficacy in vitro. British Journal of Cancer. 1999 June;80(7):998-1004.

Glerum D M, Shtanko A, Tzagoloff A, Gorman N, Sinclair P R. Cloning and identification of HEM 14, the yeast gene for mitochondrial protoporphyrinogen oxidase. Yeast. 1996 November;12(14):1421-5.

Gourley D G, Schuttelkopf A W, Leonard G A, Luba J, Hardy L W, Beverley S M, Hunter W N. Pteridine reductase mechanism correlates pterin metabolism with drug resistance intrypanosomatid parasites. National Structure Biology. 2001 June;8(6):521-5.

Goyard S, Beverley S M. Blasticidin resistance: a new independent marker for stable transfection of *Leishmania*. Mol Biochem Parasitol. 2000; 108:249-52.

Gramiccia M, Gradoni L, Troiani M. HIV-*Leishmania* co-infections in Italy. Isoenzyme characterization of *Leishmania* causing visceral leishmaniasis in HIV patients. Trans R Soc Trop Med Hyg. 1992; 86:161-3.

Gumy A, Louis J A, Launois P. The murine model of infection with *Leishmania major* and its importance for the deciphering of mechanisms underlying differences in Th cell differentiation in mice from different genetic backgrounds. Int J Parasitol. 2004; 34:433-44.

Harth Y, Hirshowitz B, Kaplan B. Modified topical photodynamic therapy of superficial skin tumors utilizing aminolevulinic acid, penetration enhancers, red light, and hyperthermia. Dermatol Surg. 1998; 24:723-6.

Hodgkinson V H, Soong L, Duboise S M, McMahon-Pratt D. *Leishmania amazonensis*: cultivation and characterization of Axenic amastigote-like organisms. Exp Parasitol. 1996; 83:94-105.

Houde M, Bertholet S, Gagnon E, Brunet S, Goyette G, Laplante A, Princiotta M F, Thibault P, Sacks D, Desjardins M. Phagosomes are competent organelles for antigen cross-presentation. Nature. 2003; 425:402-6.

Ilg T, Demar M, Harbecke D. Phosphoglycan repeat-deficient *Leishmania mexicana* parasites remain infectious to macrophages and mice. J Biol. Chem. 2001; 276:4988-97.

Joshi P B, Webb J R, Davies J E, McMaster W R. The gene encoding streptothricin acetyltransferase (sat) as a selectable marker for *Leishmania* expression vectors. Gene. 1995; 156:145-9.

Kamhawi S, Belkaid Y, Modi G, Rowton E, Sacks D. Protection against cutaneous leishmaniasis resulting from bites of uninfected sand flies. Science. 2000; 290:1351-4

Kappas A, Song C S, Sassa S, Levere R D, Granick S. The occurrence of substances in human plasma capable of inducing the enzyme delta-aminolevulinate synthetase in liver cells. Proc Natl Acad Sci USA. 1969; 64:557-64.

Kawazu S, Lu H G, Chang K P. Stage-independent splicing of transcripts two heterogeneous neighboring genes in *Leishmania amazonensis*. Gene. 1997; 196:49-59.

Kaye P M, Coburn C, McCrossan M, Beverley S M. Antigens targeted to the *Leishmania* phagolysosome are processed for CD4+ T cell recognition. European Journal of Immunology. 1993 September;23(9):2311-9.

Kurlandzka A, Zoladek T, Rytka J, Labbe-Bois R. The alternative pathway of haem synthesis via dehydroisocoproporphyrinogen in mutants of *Saccharomyces cerevisiae* partially deficient in uroporphyrinogen decarboxylase activity. Biochemistry Journal. 1991 Jan. 1;273(Pt 1):246-7.

Lane N. New light on medicine. Scientific American. January 2003; pp. 38-45.

LeBowitz J H, Cruz A, Beverley S M. Thymidine kinase as a negative selectable marker in *Leishmania major*. Molecular Biochemistry Parasitology. 1992 April;51(2):321-5

LeBowitz J H, Coburn C M, McMahon-Pratt D, Beverley S M. Development of a stable *Leishmania* expression vector and application to the study of parasite surface antigen genes. Proceedings of the National Academy of Science USA. 1990 December;87(24):9736-40.

Liu X, Chang K P. The 63-kilobase circular amplicon of tunicamycin-resistant *Leishmania amazonesis* contains a functional N-acetylglucosamine-1-phosphate transferase gene that can be used as a dominant selectable marker in transfection. Mol Cell Biol. 1992; 12:4112-22.

Lipoldova M, Svobodova M, Havelkova H, Krulova M, Badalova J, Nohynkova E, Hart A A, Schlegel D, Volf P, Demant P. Mouse genetic model for clinical and immunological heterogeneity of leishmaniasis. Immunogenetics. 2002; 54:174-83.

Locksley R M, Heinzel F P, Sadick M D, Holaday B J, Gardner K D Jr. Murine cutaneous leishmaniasis: susceptibility correlates with differential expansion of helper T-cell subsets. Ann Inst Pasteur Immunol. 1987; 138:744-9.

Melby P C, Chandrasekar B, Zhao W, Coe J E. The hamster as a model of human visceral leishmaniasis: progressive disease and impaired generation of nitric oxide in the face of a prominent Th1-like cytokine response. J. Immunol. 2001; 166:1912-20.

Mollenkopf H, Dietrich G, Kaufmann S H. Intracellular bacteria as targets and carriers for vaccination. Biological Chemistry. 2001 April;382(4):521-32.

Morris R V, Shoemaker C B, David J R, Lanzaro G C, Titus R G. Sandfly maxadilan exacerbates infection with *Leishmania major* and vaccinating against it protects against *L. major* infection. J. Immunol. 2001; 167:5226-30.

Nadim A, Javadian E, and Mohebali M. The experience of leishmanization in the Islamic Republic of Iran. La Revue de Sante de la Mediterranee orientale. 1997; 3:284-89.

Olobo J O, Gicheru M M, Anjili C O. The African green monkey model for cutaneous and visceral leishmaniasis. Trends Parasitol. 2001; 17:588-92.

Pacheco R S, Ferreira M S, Machado M I, Brito C M, Pires M Q, Da-Cruz A M, Coutinho S G. Chagas' disease and HIV co-infection: genotypic characterization of the *Trypanosoma cruzi* strain. Mem Inst Oswaldo Cruz. 1998; 93:165-9.

Papadopoulou B, Roy G, Breton M, Kundig C, Dumas C, Fillion I, Singh A K, Olivier M, Ouellette M. Reduced infectivity of a *Leishmania donovani* biopterin transporter genetic mutant and its use as an attenuated strain for vaccination. Infections and Immunology. 2002 January;70(1):62-8.

Peng Q, Warloe T, Berg K, Moan J, Kongshaug M, Giercksky K E, Nesland J M. 5-Aminolevulinic acid-based photodynamic therapy. Clinical research and future challenges. Cancer. 1997 Jun. 15;79(12):2282-308.

Probst R J, Wellde B T, Lawyer P G, Stiteler J S, Rowton E D. Rhesus monkey model for *Leishmania major* transmitted by *Phlebotomus papatasi* sandfly bites. Med Vet Entomol. 2001; 15:12-21.

Reed S G. Leishmaniasis vaccination: targeting the source of infection. J Exp Med. 2001; 194:F7-F9.

Requena J M, Soto M, Doria M D, Alonso C. Immune and clinical parameters associated with "*Leishmania infantum*" infection in the golden hamster model. Vet Immunol Immunopathol. 2000; 76:269-81.

Rozental S, de Carvalho T U, de Souza W. Influence of the endosymbiont on the interaction of *Crithidia deanei* with macrophages. Microsc Electron Biol Cel. 1987; 11:167-79.

Sah J F, Ito H, Kolli B K, Peterson D A, Sassa S, Chang K P. Genetic rescue of *Leishmania* deficiency in porphyrin biosynthesis creates mutants suitable for analysis of cellular events in uroporphyria and for photodynamic therapy. J Biol. Chem. 2002; 277:14902-9.

Sassa S. Delta-aminolevulinic acid dehydratase assay. Enzyme. 1982; 28:133-45.

Sassa S. Hematologic aspects of the porphyrias. International Journal of Hematology. 2000 January;71(1):1-17.

Sassa S, Granick S, Bickers D R, Bradlow H L, Kappas A. A microassay for uroporphyrinogen I synthase, one of three abnormal enzyme activities in acute intermittent porphyria, and its application to the study of the genetics of this disease. Proc Natl Acad Sci U.S. A. 1974; 71:732-6.

Sassa S, Nagai T. The role of heme in gene expression. International Journal of Hematology. 1996 April;63 (3): 167-78.

Scott P, Natovitz P, Coffman R L, Pearce E, Sher A. Immunoregulation of cutaneous leishmaniasis. T cell lines that transfer protective immunity or exacerbation belong to different T helper subsets and respond to distinct parasite antigens. J Exp Med. 1988; 168:1675-84.

Shaw J J. Taxonomy of the genus *Leishmania*: present and future trends and their implications. Mem Inst Oswaldo Cruz. 1994; 89:471-8.

Somanna A, Mundodi V, Gedamu L. Functional analysis of cathepsin B-like cysteine proteases from *Leishmania donovani* complex. Evidence for the activation of latent transforming growth factor beta. J Biol. Chem. 2002; 277: 25305-12.

Spath G F, Garraway L A, Turco S J, Beverley S M. The role(s) of lipophosphoglycan (LPG) in the establishment of *Leishmania major* infections in mammalian hosts. Proc Natl Acad Sci USA. 2003; 100:9536-41

Spath G F, Lye L F, Segawa H, Sacks D L, Turco S J, Beverley S M. Persistence without pathology in phosphoglycan-deficient *Leishmania major*. Science. 2003; 301: 1241-3.

Spath G F, Lye L F, Segawa H, Turco S J, Beverley S M. Identification of a compensatory mutant (lpg2-REV) of *Leishmania major* able to survive as amastigotes within macrophages without LPG2-dependent glycoconjugates and its significance to virulence and immunization strategies. Infect Immun. 2004; 72:3622-7.

Spikes J D, Bommer J C. Photosensitizing properties of mono-L-aspartyl chlorin e6 (NPe6): a candidate sensitizer for the photodynamic therapy of tumors. Journal of Photochemistry and Photobiology B. 1993 February;17(2):135-43.

Strelkova M V. Susceptibility to and the characteristics of the course of experimental leishmaniasis in different species of mammals infected with *Leishmania major, L. turanica* and *L. gerbilli* Medarazitol (Mosk). 1991; (1):35-9.

Tamar S, Dumas C, Papadopoulou B. Chromosome structure and sequence organization between pathogenic and non-pathogenic *Leishmania* spp. Mol Biochem Parasitol. 2000; 111:401-14.

Taylor E L, Brown S B. The advantages of aminolevulinic acid photodynamic therapy in dermatology. Journal of Dermatological Treatment. 2002;13 Suppl 1:S3-11.

Tetaud E, Lecuix I, Sheldrake T, Baltz T, Fairlamb A H. A new expression vector for Crithidia fasciculata and *Leishmania*. Molecular Biochemistry and Parasitology. 2002 Apr. 9;120(2):195-204.

Titus R G, Gueiros-Filho F J, de Freitas L A, Beverley S M. Development of a safe live *Leishmania* vaccine line by gene replacement. Proc Natl Acad Sci USA. 1995; 92:10267-71.

Valenzuela J G, Belkaid Y, Garfield M K, Mendez S, Kamhawi S, Rowton E D, Sacks D L, Ribeiro J M. Toward a defined anti-*Leishmania* vaccine targeting vector antigens: characterization of a protective salivary protein. J Exp Med. 2001; 194:331-42.

Wainwright M. Photodynamic antimicrobial chemotherapy (PACT). Journal of Antimicrobial Chemother. 1998 July;42(1):13-28.

Wang W, Boynton J E, Gillham N W. Genetic control of chlorophyll biosynthesis in chlamydomonas: analysis of a mutant affecting synthesis of delta-aminolevulinic acid. Cell. 1975 September;6(1):75-84.

Zhang K, Showalter M, Revollo J, Hsu F F, Turk J, Beverley S M. Sphingolipids are essential for differentiation but not growth in *Leishmania*. EMBO J. 2003; 22:6016-26.

What is claimed is:

1. A method for vaccinating a vertebrate subject against leishmaniasis, the method comprising:
   providing a live mutant *Leishmania* having been modified to have δ-aminolevulinate dehydratase (ALAD) activity and porphobilinogen deaminase (PBGD) activity and further having a phenotype of:
   (a) δ-aminolevulinate synthase-negative; and
   (b) negative for at least one heme biosynthetic pathway enzymes selected from the group consisting of uroporphyrinogen cosynthase, uroporphyrinogen decarboxylase, coproporhyrinogen oxidase, protopophyrinogen oxidase and ferrochelatase;
   exposing the live mutant *Leishmania* to δ-aminolevulinate to produce a porphyric *Leishmania* without lysing the *Leishmania* either before or after administering the *Leishmania* to the vertebrate subject; administering the live mutant *Leishmania* to the vertebrate subject;
   exposing the *Leishmania* to white or red light to lyse the porphyric *Leishmania* to release antigens from the *Leishmania* to initiate an immune response by the subject.

2. The method of claim 1, wherein the vertebrate subject is a mammal.

3. The method of claim 1, wherein the vertebrate subject is human.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: Artificial primer sequence

<400> SEQUENCE: 1
tgcccactgg atccccgcca tg    22

<210> SEQ ID NO 2
<211> LENGTH: 22
<212> TYPE: DNA
<213> ORGANISM: Artificial
<220> FEATURE:
<223> OTHER INFORMATION: Artificial primer sequence

<400> SEQUENCE: 2
cactgggatc catcattcct cc    22